(12) United States Patent
Tojo et al.

(10) Patent No.: US 9,637,466 B2
(45) Date of Patent: May 2, 2017

(54) LIQUID CRYSTAL COMPOUND HAVING 2, 6-DIFLUOROPHENYL ETHER STRUCTURE AND LIQUID CRYSTAL COMPOSITION THEREOF

(71) Applicant: DIC CORPORATION, Tokyo (JP)

(72) Inventors: Kenta Tojo, Kitaadachi-gun (JP); Tetsuo Kusumoto, Kitaadachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 14/904,226

(22) PCT Filed: Jul. 15, 2014

(86) PCT No.: PCT/JP2014/068784
§ 371 (c)(1),
(2) Date: Jan. 11, 2016

(87) PCT Pub. No.: WO2015/012156
PCT Pub. Date: Jan. 29, 2015

(65) Prior Publication Data
US 2016/0152589 A1 Jun. 2, 2016

(30) Foreign Application Priority Data

Jul. 25, 2013 (JP) ................................ 2013-154499

(51) Int. Cl.
C07D 319/06 (2006.01)
C09K 19/04 (2006.01)
C09K 19/34 (2006.01)

(52) U.S. Cl.
CPC ........ *C07D 319/06* (2013.01); *C09K 19/0403* (2013.01); *C09K 19/3402* (2013.01); *C09K 2019/3422* (2013.01)

(58) Field of Classification Search
CPC .................................................. C07D 319/06
See application file for complete search history.

(56) References Cited

U.S. PATENT DOCUMENTS

| | | | |
|---|---|---|---|
| 5,032,313 | A | 7/1991 | Goto et al. |
| 5,324,449 | A | 6/1994 | Kurmeier et al. |
| 5,487,845 | A | 1/1996 | Reiffenrath et al. |
| 6,200,654 | B1 | 3/2001 | Poetsch et al. |
| 6,210,603 | B1 | 4/2001 | Kondo et al. |
| 6,579,577 | B2 | 6/2003 | Kondo et al. |
| 8,916,718 | B2 | 12/2014 | Tojo et al. |
| 9,079,836 | B2 | 7/2015 | Tojo et al. |
| 9,181,484 | B2 | 11/2015 | Tojo et al. |
| 9,315,727 | B2 | 4/2016 | Tojo et al. |
| 2002/0166994 | A1 | 11/2002 | Kondo et al. |
| 2003/0236304 | A1 | 12/2003 | Jolidon et al. |
| 2005/0017216 | A1 | 1/2005 | Poetsch et al. |
| 2005/0092966 | A1 | 5/2005 | Heckmeier et al. |
| 2006/0263542 | A1 | 11/2006 | Kirsch et al. |
| 2007/0051919 | A1 | 3/2007 | Kondou et al. |
| 2009/0065739 | A1 | 3/2009 | Haseba et al. |
| 2009/0302273 | A1 | 12/2009 | Tanaka |
| 2010/0127211 | A1 | 5/2010 | Tanaka |
| 2010/0328600 | A1 | 12/2010 | Shimada et al. |

(Continued)

FOREIGN PATENT DOCUMENTS

| | | |
|---|---|---|
| CN | 102186821 A | 9/2011 |
| JP | 2-501311 A | 5/1990 |
| JP | 2-233626 A | 9/1990 |

(Continued)

OTHER PUBLICATIONS

International Search Report dated Oct. 7, 2014, issued in counterpart Application No. PCT/JP2014/068784 (3 pages).

(Continued)

*Primary Examiner* — Noble Jarrell
*Assistant Examiner* — John S Kenyon
(74) *Attorney, Agent, or Firm* — Westerman, Hattori, Daniels & Adrian, LLP

(57) ABSTRACT

The present invention relates to a compound having 2,6-difluorophenyl ether structure and useful as an organic electronic material and a medicine/agrochemical, particularly a material for liquid crystal display devices, and also relates to an effective method for producing the same. The present invention provides a compound represented by general formula (1)

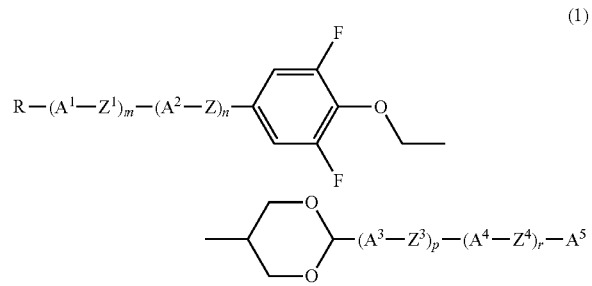

and also provides a liquid crystal composition containing the compound and a liquid crystal display device using the liquid crystal composition.

A liquid crystal composition exhibiting low viscosity and a liquid crystal phase within a wide temperature range can be produced by using the compound represented by the general formula (1) as a component of the liquid crystal composition. Thus, the compound is very useful as a constituent component of a liquid crystal composition for a liquid crystal display device required to have, fast response.

10 Claims, 1 Drawing Sheet

(56) References Cited

U.S. PATENT DOCUMENTS

2011/0193022 A1   8/2011   Tanaka et al.

FOREIGN PATENT DOCUMENTS

| | | |
|---|---|---|
| JP | 4-501575 A | 3/1992 |
| JP | 6-504032 A | 5/1994 |
| JP | 3-157202 A | 6/1997 |
| JP | 10-101599 A | 4/1998 |
| JP | 2000-355560 A | 12/2000 |
| JP | 2001-019649 A | 1/2001 |
| JP | 2004-352721 A | 12/2004 |
| JP | 2004-355560 A | 12/2004 |
| JP | 2005-517079 A | 6/2005 |
| JP | 2005-529176 A | 9/2005 |
| JP | 2007-070295 A | 3/2007 |
| JP | 2009-067780 A | 3/2009 |
| JP | 5-263461 B2 | 8/2013 |
| JP | 2013-170246 A | 9/2013 |
| JP | 5-382268 B1 | 1/2014 |
| JP | 5435318 B1 | 3/2014 |
| JP | 2014-105178 A | 6/2014 |
| KR | 10-2006-0119879 A | 11/2006 |
| WO | 98/23564 A1 | 6/1998 |
| WO | 2005/019377 A1 | 3/2005 |
| WO | 2008/105286 A1 | 9/2008 |
| WO | 2009/034867 A1 | 3/2009 |
| WO | 2009/150963 A1 | 12/2009 |
| WO | 2010/047260 A1 | 4/2010 |
| WO | 2012/161178 A1 | 11/2012 |
| WO | 2013/018796 A1 | 2/2013 |
| WO | 2013/099754 A1 | 7/2013 |
| WO | 2013/141116 A1 | 9/2013 |
| WO | 2013/172162 A1 | 11/2013 |

OTHER PUBLICATIONS

Written Opinion dated Oct. 7, 2014, issued in counterpart Application No. PCT/JP2014/068784 (4 pages).
Notification of Reason for Refusal dated Jan. 29, 2015, issued in Japanese Patent Application No. 2014-556873, w/English translation (7 pages).
ntemational Search Report dated Aug. 6, 2013, issued in PCT/JP2013/062077.
Decision to Grant a Patent for JP2013-544601, mailing date of Nov. 14, 2013.
Written Opinion dated Dec. 10, 2013, issued in counterpart Application No. PCT/JP2013/075266.
International Search Report dated Apr. 2, 2013, issued in counterpart Application No. PCT/JP2012/083070.
Kuchar, Miroslav, et al., "Use of QSAR in Design of Antiinflammatory Fluorinated Arylalkanoic Acids", Collection of Czechoslovak Chemical Communications, 1990, vol. 55, No. 1, pp. 296-306.
Resistry(stn) [Online], Oct. 3, 2011 (Oct. 3, 2011), (retrieval date: Mar. 11, 2013 (Mar. 11, 2013)) CAS resistration No. 1334226-61-7.
International Search Report dated Oct. 7, 2014, issued in counterpart Application No. PCT/JP2014/072633.
International Search Report dated Dec. 10, 2013, issued in counterpart Application No. PCT/JP2013/075266.
Written Opinion dated Oct. 7, 2014, issued in counterpart Application No. PCT/JP2014/072633.
Notification of Reasons for Refusal dated Jan. 29, 2015. issued in counterpart Japanese Patent Application No. 2014-556869, w/English translation.
Decision to Grant a Patent dated Apr. 2, 2015, issued in counterpart Japanese Patent Application No. 2014-556869, w/English translation.

LIQUID CRYSTAL COMPOUND HAVING 2, 6-DIFLUOROPHENYL ETHER STRUCTURE AND LIQUID CRYSTAL COMPOSITION THEREOF

TECHNICAL FIELD

The present invention relates to a compound having a 2,6-difluorophenyl ether structure useful as an organic electronic material and a medicine/agrochemical, particularly a material for liquid crystal display devices, and also relates to an effective, method for producing the same.

BACKGROUND ART

Liquid crystal display devices have been used for watches and electronic calculators, various measuring apparatuses, automotive panels, word processors, electronic notebooks, printers, computers, televisions, watches, advertising displays, etc. Typical examples of a liquid crystal display mode include a TN (twisted nematic) mode, a STN (super twisted nematic) mode, a vertical alignment mode using TFT (thin-film transistor), an IPS (in-plane switching) mode, and the like. Liquid crystal compositions used for these liquid crystal display devices are required to have stability to external factors such as moisture, air, heat, light, and the like, exhibit a liquid crystal phase (a nematic phase, a smectic phase, a blue, phase, and the like) within as wide a temperature range as possible including room temperature as a center, and have low viscosity and low drive voltage. Further, each of the liquid crystal compositions is composed of several types to several tens types of compounds selected for giving optimum values of dielectric anisotropy ($\Delta\epsilon$) and refractive index anisotropy ($\Delta n$) for a display device.

A horizontal alignment-mode display such as a TN mode, a STN mode, or an IPS mode uses a liquid crystal composition having positive $\Delta\epsilon$. There is also reported a driving method in which a liquid crystal composition having $\Delta\epsilon$ positive As is vertically aligned with no voltage applied, and a display is realized by applying a transverse, electric field, and the necessity for a liquid crystal composition having positive $\Delta\epsilon$ is further increased. On the other hand, an improvement in response speed is required for all driving methods, and a liquid composition having lower viscosity than present is required for solving this problem. In order to produce a liquid crystal composition having low viscosity, it is effective to decrease the viscosity of each of polar compounds constituting the liquid crystal composition. Also, when a liquid crystal composition is used for a display device or the like, it is required for the liquid crystal composition to exhibit a stable nematic phase within a wide temperature range. In order to maintain a nematic phase within a wide temperature range, each of the components constituting the liquid crystal composition is required to have high miscibility with other components and a high clearing pint ($T_{\to i}$).

In order to produce a compound having high $T_{\to i}$, it is known to be preferred to introduce, three or more ring structures such as a 1,4-cyclohexylene group or 1,4-phenylene group. On the other hand, in order to produce a compound having low viscosity, a compound having a plurality of ring structures directly connected to each other without through a connecting group, that is, a compound called a directly-connected ring system, is considered to be preferred. However, a directly-connected ring system compound having three or more ring structures and positive $\Delta\epsilon$ generally has high crystallinity and often has low miscibility in a liquid crystal composition. In order to resolve this problem, compounds having various connecting groups introduced therein have been investigated. It becomes clear that viscosity is slightly increased by introducing a connecting group, but miscibility in a liquid crystal composition can be improved (Patent Literatures 1 to 8). However, a molecule having e connecting group generally has high viscosity and the problem of significantly decreasing $T_{\to i}$. Patent Literature 9 gescribes a compound below as a compound having low viscosity and high miscibility in a liquid crystal composition. However, the compound does not have satisfactorily high $T_{\to i}$.

[Chem. 1]

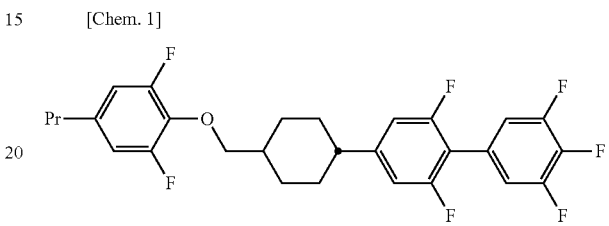

CITATION LIST

Patent Literature

PTL 1: Japanese Unexamined Patent Application Publication No. 10-101599

PTL 2: Japanese Unexamined Patent Application Publication (Translation of PCT Publication) No. 2-501311

PTL 3: Japanese Unexamined Patent Application Publication No. 9-157202

PTL 4: Japanese Unexamined Patent Application Publication (Translation of PCT Publication) No. 2005-517079

PTL 5: Japanese Unexamined Patent Application Publication No. 2-233626

PTL 6: Japanese Unexamined Patent Application Publication (Translation of PCT Publication) No. 4-501575

PTL: Japanese Unexamined Patent Application Publication (Translation of PCT Publication) No. 6-504032

PTL 8: WO 98/23564

PTL 9: WO 2012/161178

SUMMARY OF INVENTION

Technical Problem

A problem to be solved by the present invention is to provide a compound having high $\Delta\epsilon$, relatively high $T_{\to i}$, low viscosity ($\eta$), and high miscibility with other liquid crystal compounds, and also provide a liquid crystal composition containing the compound as a constituent member and to liquid crystal display device.

Solution to Problem

As a result of investigation of various compounds for solving the problem, the inventors found that the problem can be effectively solved by a compound having both a 2,6-difluorophenyl ether structure and a 1,3-dioxane ring, leading to the achievement of the present invention.

The present invention provides a compound represented by general formula (1),

[Chem. 2]

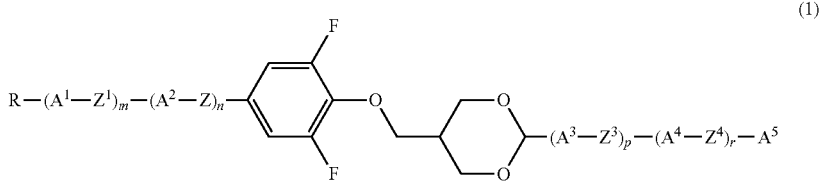

(1)

(in the formula, R represents an alkyl group having 1 to 15 carbon atoms or an alkenyl group having 2 to 15 carbon atoms, one —$CH_2$— or two or more unadjacent —$CH_2$— present in the group may be substituted by —O—, —S—, —COO—, —OCO—, or —CO—, and a hydrogen atom present in the group may be substituted by a fluorine atom, $A^1$, $A^2$, $A^3$, and $A^4$ each independently represent a group selected from the group consisting of (a) a 1,4-cyclohexylene group (one —$CH_2$— or two or more unadjacent —$CH_2$— present in the group may be substituted by —O— or —S—);

(b) a 1,4-phenylene group (one —CH= or two or more unadjacent —CH= present in the group may be substituted by —N=, and a hydrogen atom present in the group may be substituted by a fluorine atom); and (c) a naphthalene-2,6-dienyl group (a hydrogen atom present in the group may be substituted by a fluorine atom), $Z^1$, $Z^2$, $Z^3$, and $Z^4$ each independently represent —$CH_2O$—, —$OCH_2$—, —$CF_2O$—, —$OCF_2$—, —$CH_2CH_2$—, —$CF_2CF_2$—, —CH=CH—, —CF=CF—, —C≡C—, or a single bond,
$A^5$ represents

[Chem. 3]

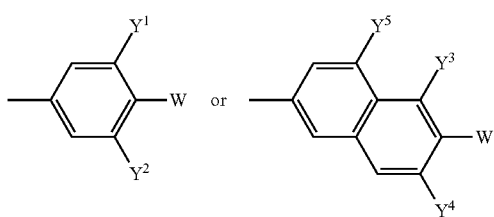

(in the formula, W represents a fluorine atom, a chlorine atom, a cyano group, —$CF_3$, —$OCH_2F$, —$OCF_2$, or —$OCF_3$, and $Y^1$, $Y^2$, $Y^3$, $Y^4$, and $Y^5$ each independently represent a fluorine atom, a chlorine atom, or a hydrogen atom), m, n, p, and r each independently represent 0 or 1, and m+n+p+r is 0, 1, 2, or 3, and also present invention provides a liquid crystal composition containing the compound and a liquid crystal display device using the liquid crystal composition.

Advantageous Effects of Invention

A novel liquid crystal compound provided by the present invention and represented by the general formula (1) can be easily industrially produced, and the resultant compound represented by the general formula (1) has relatively large Δ∈, relatively high $T_{→i}$, low viscosity, and high miscibility in a liquid crystal composition.

Therefore, a liquid crystal composition exhibiting to viscosity and a liquid crystal phase within a wide temperature range, can be produced by using the compound represented by the general formula (1) as a component of the liquid crystal composition. Thus the compound is very useful as a constituent component of a liquid crystal composition for a liquid crystal display device required to have fast response.

DESCRIPTION OF EMBODIMENTS

Figure 1:
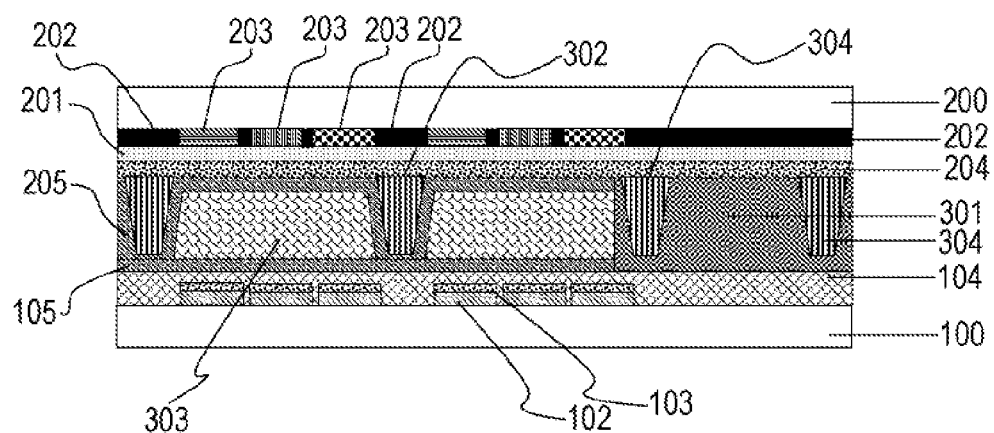
FIG. 1 is a sectional view of a liquid crystal display device of the present invention, in which a substrate denoted by 100 to 105 is referred to as a "back plane" and a substrate denoted by 200 to 205 is referred to as a "front plane".
Figure 2:
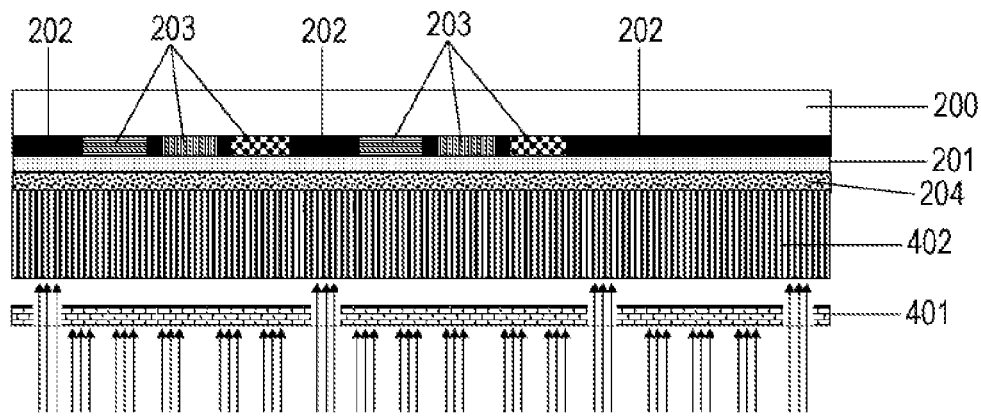
FIG. 2 is a drawing of an exposure treatment step using as a photomask pattern a pattern for forming columnar spacers on a black matrix.

In the general formula (1), in order to decrease viscosity, R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms. Also R is preferably linear.

In order to decrease viscosity, $A^1$, $A^2$, $A^3$, and $A^4$ are preferably each independently a trans-1,4-cyclohexylene group, an unsubstituted naphthalene-2,6-diyl group, or an unsubstituted 1,4-phenylene group, and more preferably a trans-1,4-cyclohexylene group; in order to increase Δ∈, $A^1$, $A^2$, $A^3$, and $A^4$ are preferably each independently

[Chem. 4]

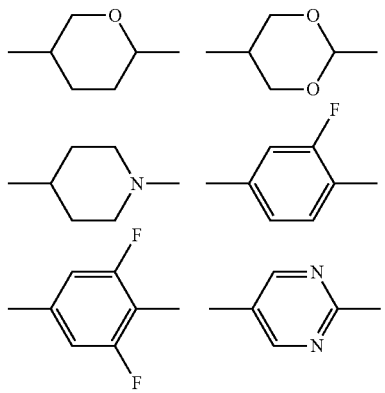

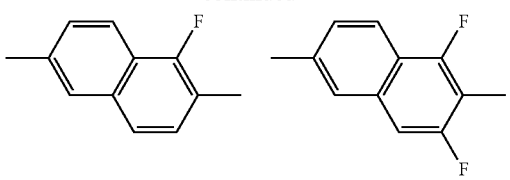

and more preferably

[Chem. 5]

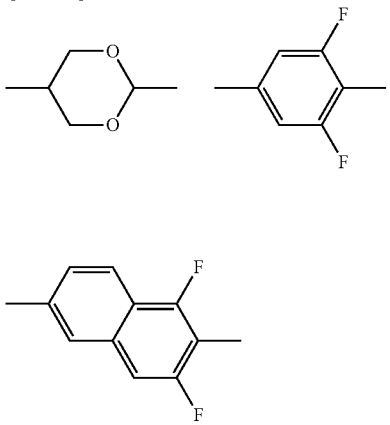

and in order to increase $T_{\rightarrow i}$, $A^1$, $A^2$, $A^3$, and $A^4$ are preferably each independently a trans-1,4-cyclohexylene group or an unsubstituted 1,4-phenylene group.

In order to decrease viscosity, $A^5$ is preferably

[Chem. 6]

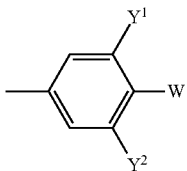

and in order to increase $T_{\rightarrow i}$,

[Chem. 7]

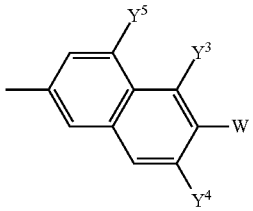

is preferred.

In order to decrease viscosity and increase $T_{\rightarrow i}$, $Y^1$, $Y^2$, $Y^3$, $Y^4$, and $Y^5$ are preferably each independently a hydrogen atom, and in order to increase $\Delta\epsilon$, $Y^1$, $Y^2$, $Y^3$, $Y^4$, and $Y^5$ are preferably each independently a fluorine atom.

When $Y^3$ to $Y^5$ are each independently a fluorine atom or a hydrogen atom, in order to increase $\Delta\epsilon$,

[Chem. 8]

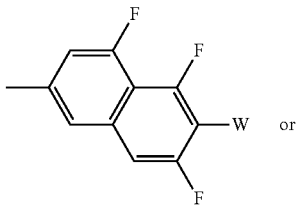

is preferred, and in order to decrease viscosity,

[Chem. 9]

is preferred.

In order to increase $\Delta\epsilon$, W is preferably a fluorine atom, a cyano group, —$CF_3$, or —$OCF_3$, and in order to decrease viscosity, W is preferably a fluorine atom.

In order to decrease viscosity, $Z^1$, $Z^2$, $Z^3$, and $Z^4$ are preferably each independently —$CH_2O$—, —$OCH_2$—, —$CF_2O$—, —$OCF_2$—, —CF=CF—, —C≡C—, or a single bond, more preferably —$CF_2O$—, —$OCF_2$—, —$CH_2CH_2$—,CH—, or a single bond, and particularly preferably a single bond, and in order to increase $T_{43\ i}$, $Z^1$, $Z^2$, $Z^3$, and $Z^4$ are preferably each independently —C≡C— or a single bond.

When η is regarded important, m+n+p+r is preferably 0 or 1, and, in particular, p and r are more preferably each 0, and when $T_{\rightarrow i}$ is regarded important, m+n+p+r is preferably 1 or 2. In order to enhance miscibility in a liquid crystal composition, m+n+p+r is preferably 0 or 1.

The compound represented by the general formula (1) does not have a structure in which heteroatoms are directly bonded to each other.

Preferred examples of the compound are given below, but the present invention is not limited to these examples. Preferred compounds of the general formula (1) include compounds represented by general formula (1a) to general formula (1j) below.

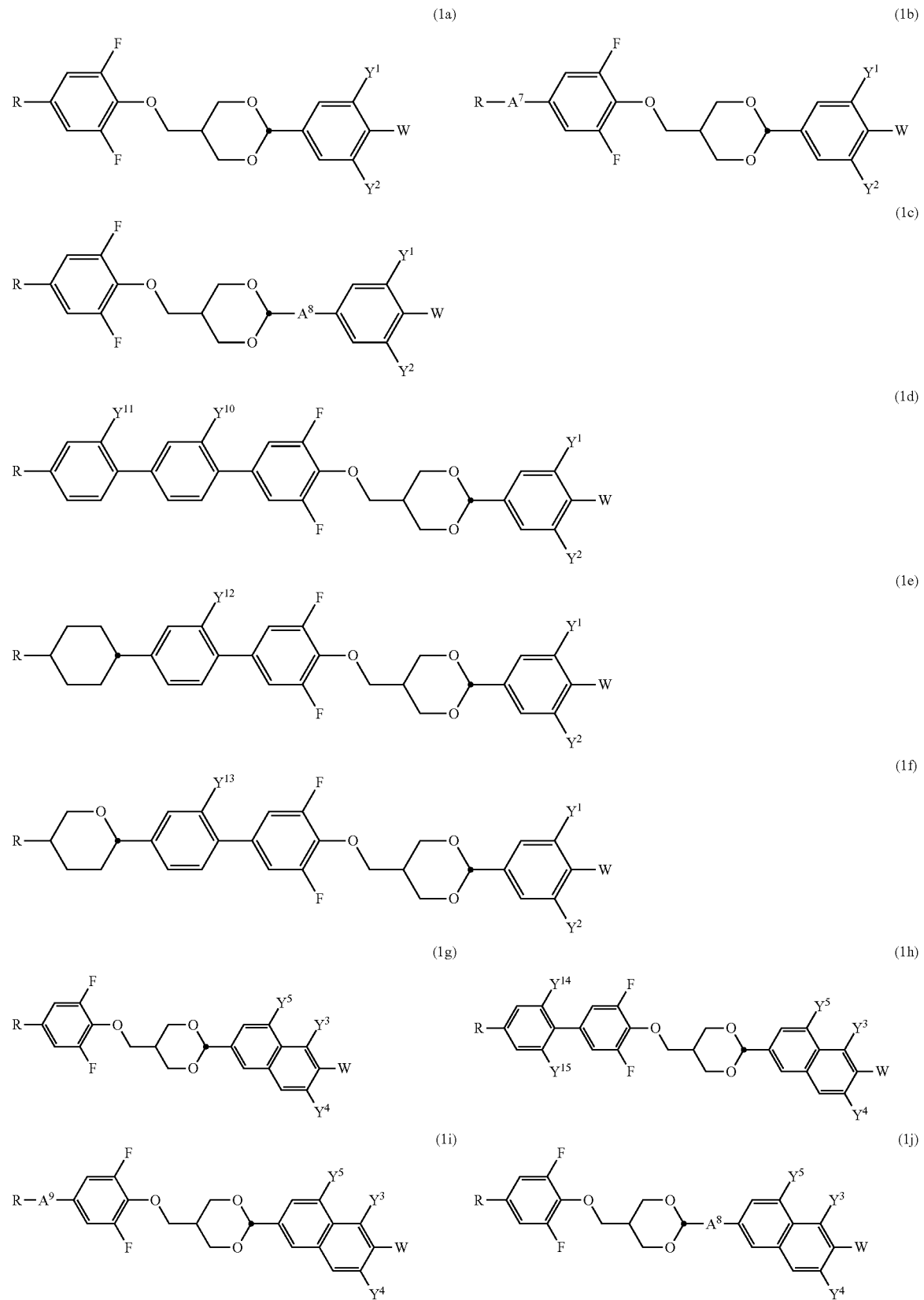

(In the formulae, R, W, $Y^1$, $Y^2$, $Y^3$, $Y^4$, and $Y^5$ each independently represent the same meaning as R, W, $Y^1$, $Y^2$, $Y^3$, $Y^4$ and $Y^5$ in the general formula (1), $Y^{10}$, $Y^{11}$, $Y^{12}$, $Y^{13}$, and $Y^{15}$ each independently represent a fluorine atom, a chlorine atom, or a hydrogen atom, and $A^7$, $A^8$, and $A^9$ each independently represent (a) a 1,4-cyclohexylene group (one —$CH_2$— or tea or more unadjacent —$CH_2$— present in the group may be substituted by —O— or —S—); or (b) a 1,4-phenylene group (one —CH= or two or more unadjacent —CN= present in the group may be substituted by —N=, and a hydrogen atom present in the group may be substituted by a fluorine atom)).

In a compound represented by the general formula (1a), R preferably represents an alkyl group having 1 to 12 carbon atoms, an alkenyl group having 2 to 12 carbon atoms, an alkoxy group having 1 to 12 carbon atoms, or an alkenyloxy group having 2 to 12 carbon atoms, more preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^1$ and $Y^2$ are preferably each independently a hydrogen atom or a fluorine atom, and W is preferably a fluorine atom, a cyano group, —$CF_3$, or —$OCF_3$. The compound represented by the general formula (1a) is more preferably a compound represented by general formula (1a-1) to general formula (1a-11) below and still more preferably a compound represented by the general formula (1a-1).

[Chem. 11]

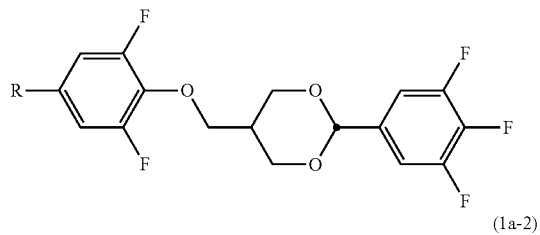
(1a-1)

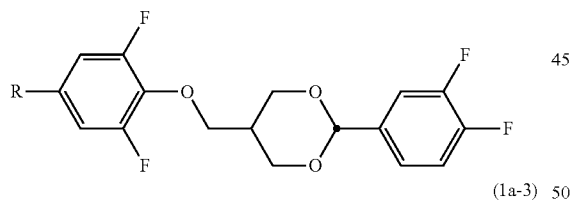
(1a-2)

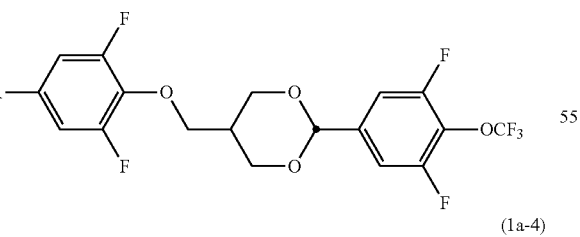
(1a-3)

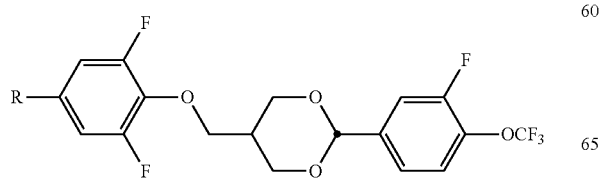
(1a-4)

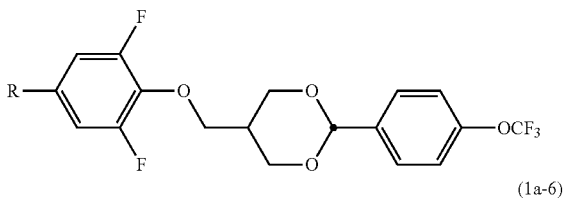
(1a-5)

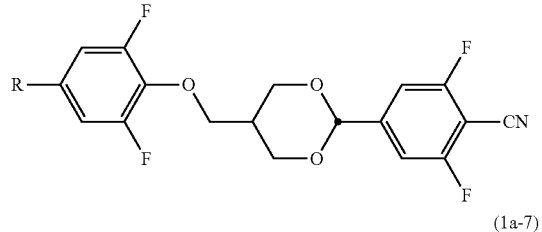
(1a-6)

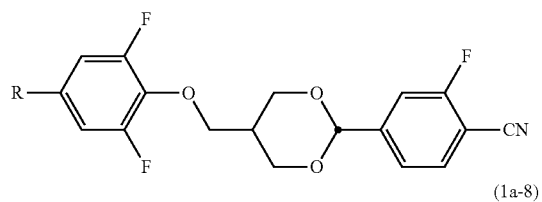
(1a-7)

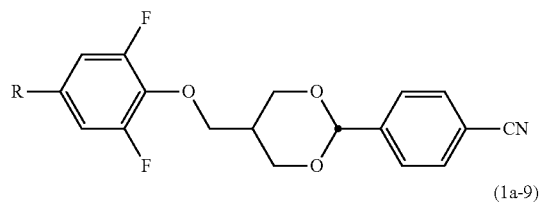
(1a-8)

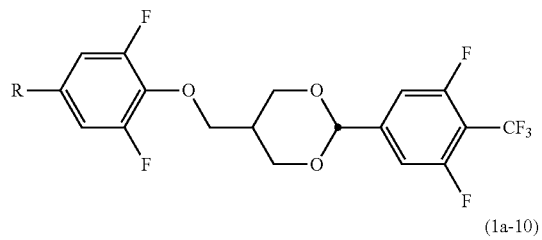
(1a-9)

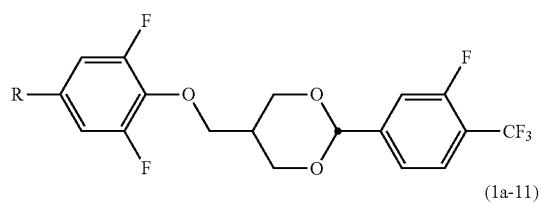
(1a-10)

(1a-11)

(in the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

In a compound represented by the general formula (1b), R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^1$, $Y^2$, $Y^6$, and $Y^7$ are preferably each independently a hydrogen atom or a fluorine atom, W is preferably a fluorine atom, a cyano group, or —$OCF_3$, and $A_7$ is preferably independently a 1,4-cyclohexylene group, a 1,4-phenylene group, or

[Chem. 12]

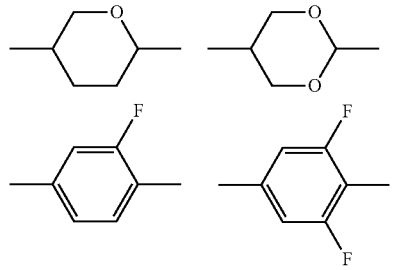

The compound represented by the general formula (1b) in which $A_7$ is a 1,4-phenylene group (one —CH= or two or more unadjacent —CH= present in the group may be substituted by —N=, and a hydrogen present in the group may be substituted by a fluorine atom) is more preferably a compound represented by general formula (1b-1) to general formula (1b-16) below.

[Chem. 13]

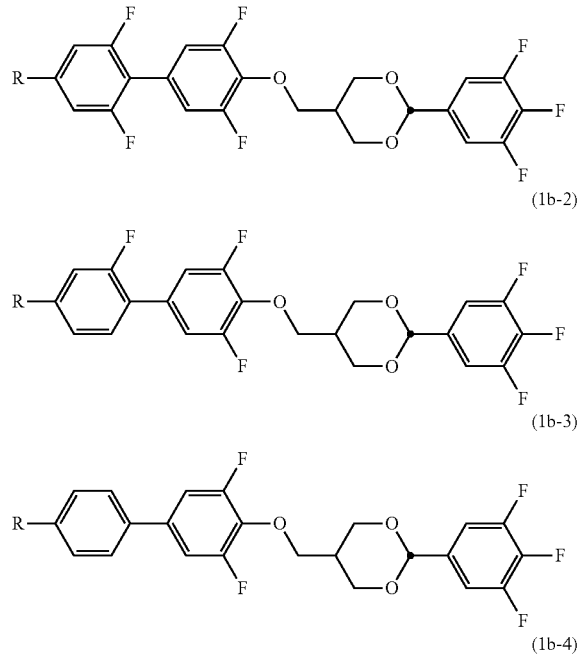

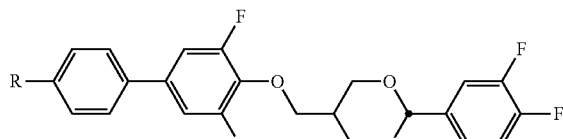
(1b-5)

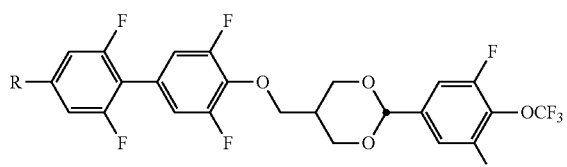
(1b-6)

(1b-7)
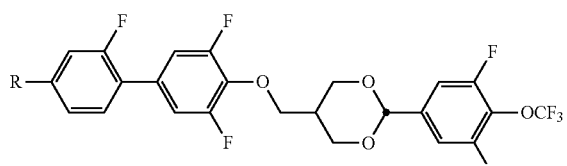

(1b-8)
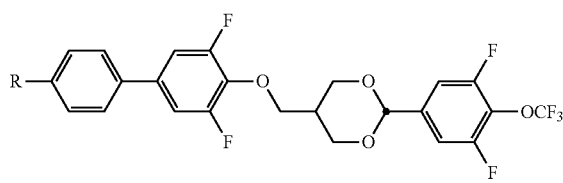

(1b-9)
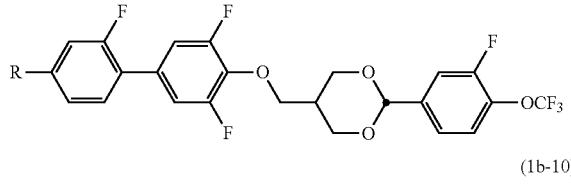

(1b-10)

(1b-11)
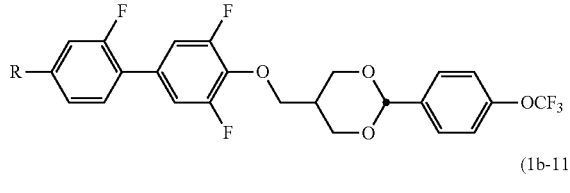

(1b-12)
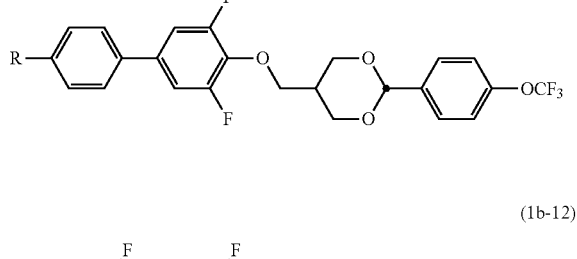

(1b-13)
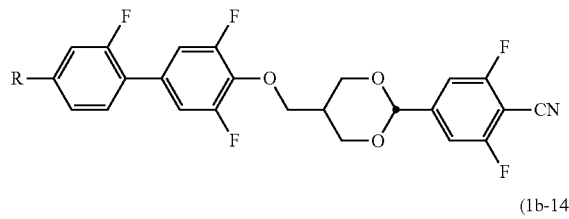

(1b-14)
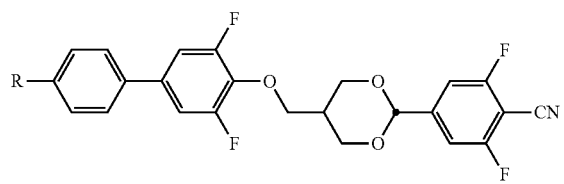

(1b-15)
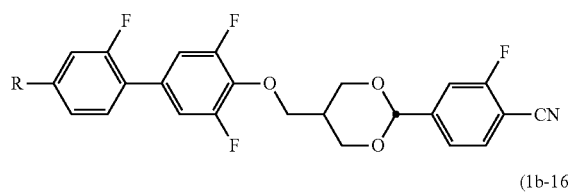

(1b-16)
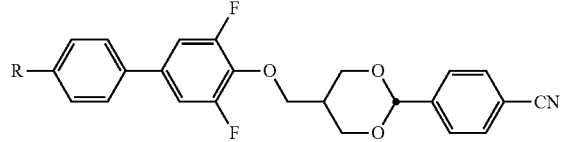

In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

The compound represented by the general formula (1b) in which A₇ is a 1,4-cyclohexylene group (one —CE₂— or two or more unadjacent —CH₇— present in the group may be substituted by —O— or —S—) is more preferably a compound represented by general formula (1b-17) to general formula (1b-32) below and.

[Chem. 14]

(1b-17)
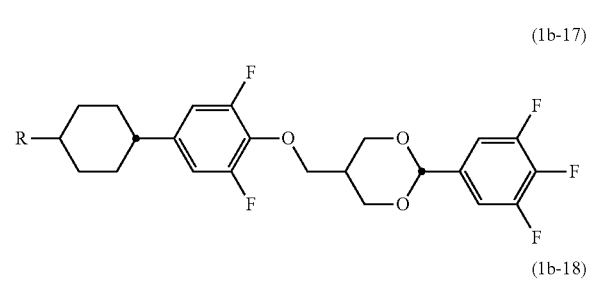

(1b-18)
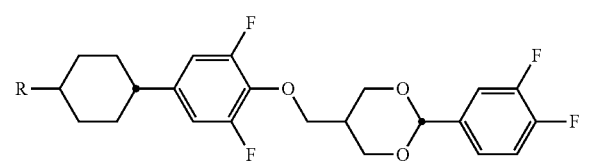

(1b-19)
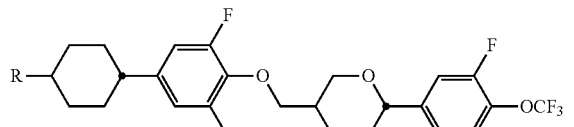

(1b-20)
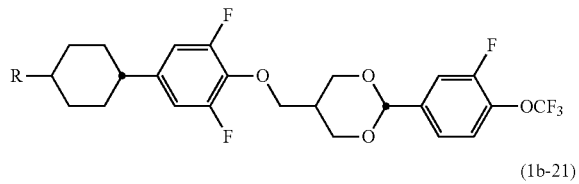

(1b-21)
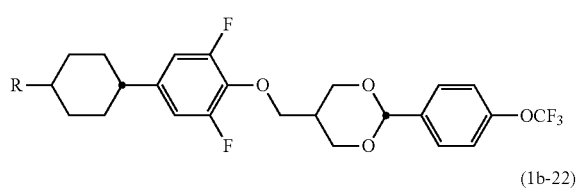

(1b-22)
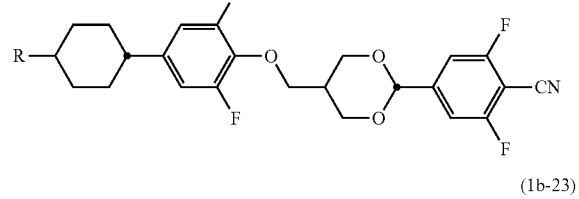

(1b-23)
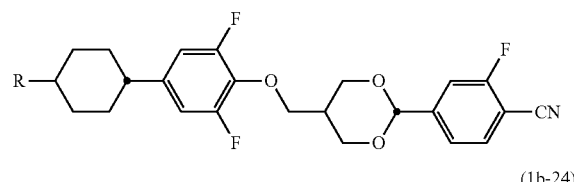

(1b-24)
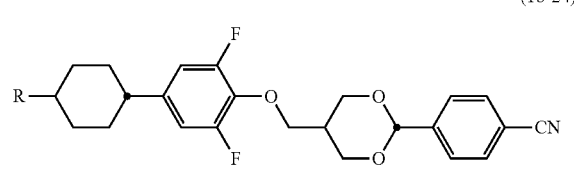

(1b-25)
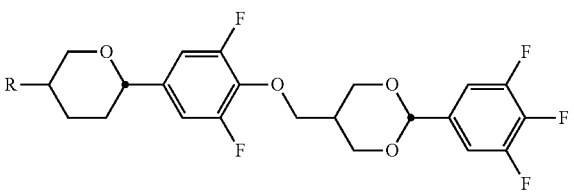

(1b-26)
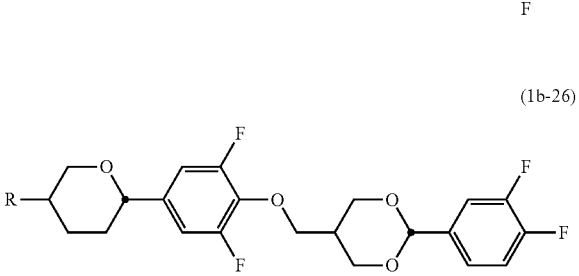

(1b-27)
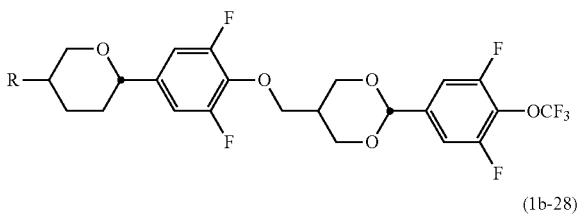

(1b-28)
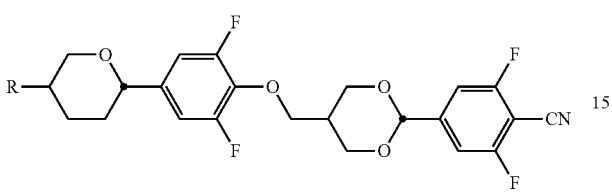

(1b-29)
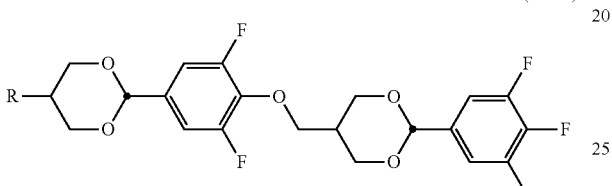

(1b-30)
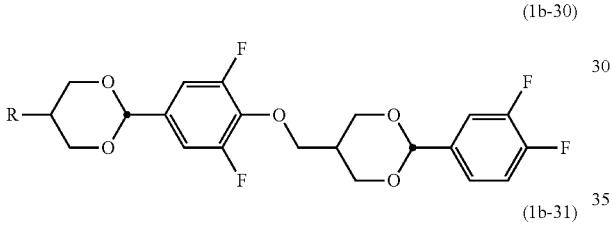

(1b-31)
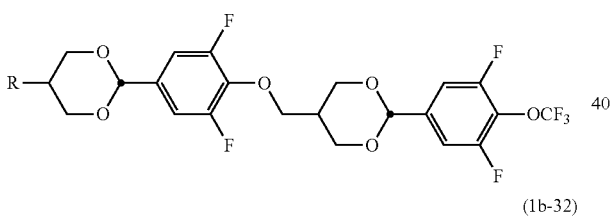

(1b-32)
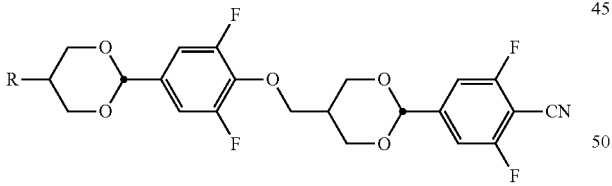

(In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

In a compound represented by the general formula (1c), R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^1$ and $Y^2$ are preferably each independently a hydrogen atom or a fluorine atom, W is preferably a fluorine atom, a cyano group, or —$OCF_3$, and $A_8$ is preferably a trans-1,4-cyclohexylene group or

[Chem. 15]
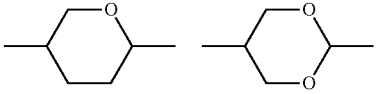

The compound represented by the general formula (1c) is more preferably a compound represented by general formula (1c-1) to general formula (1c-17) below and further preferably general formula (1c-1) to general formula (1c-3).

[Chem. 16]

(1c-1)
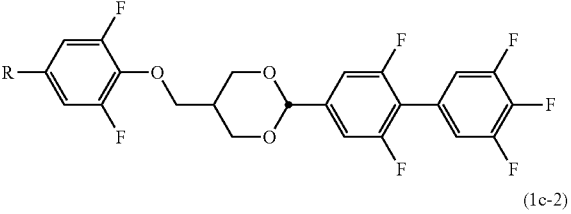

(1c-2)
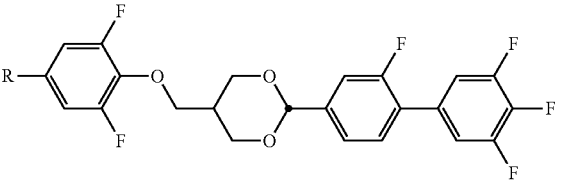

(1c-3)
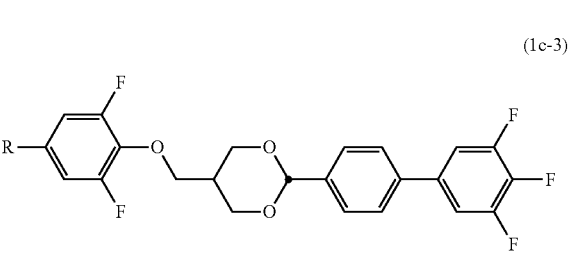

(1c-4)
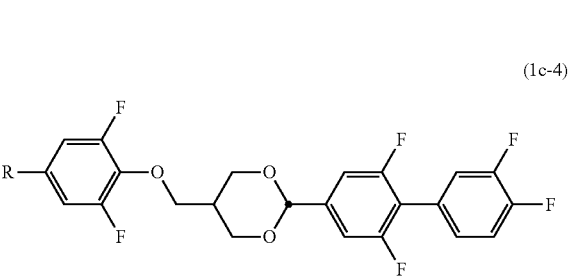

(1c-5)
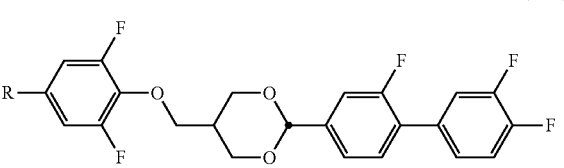

-continued (1c-6)
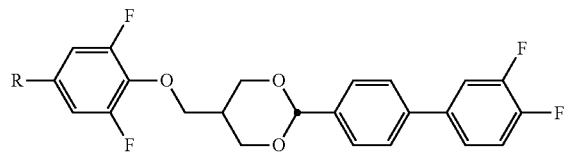

(1c-7)
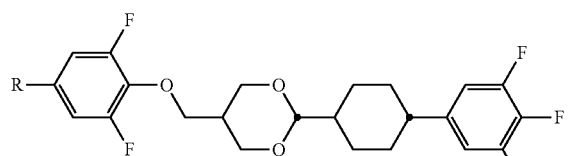

(1c-8)
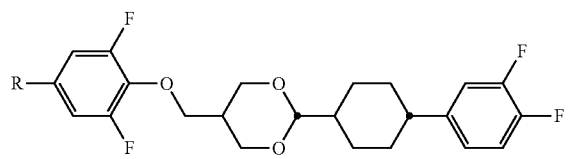

(1c-9)
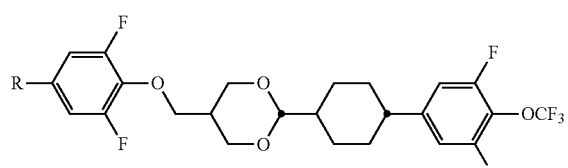

(1c-10)
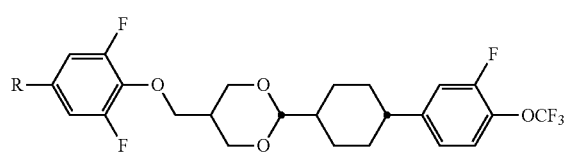

(1c-11)
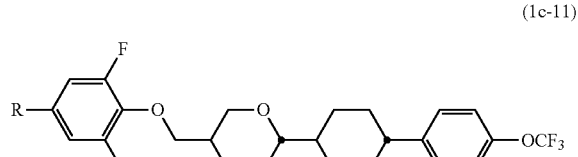

(1c-12)
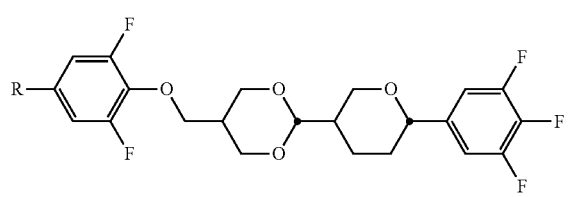

-continued (1c-13)
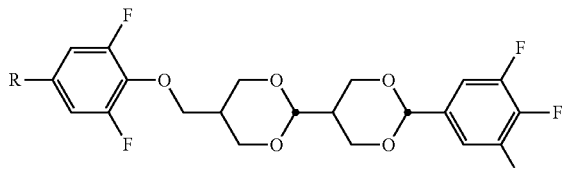

(1c-14)
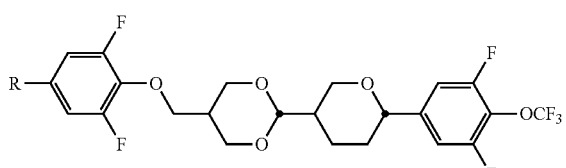

(1c-15)
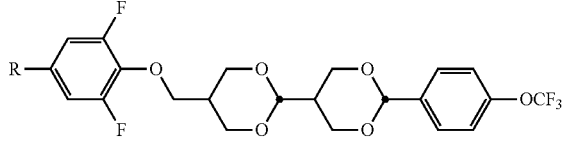

(1c-16)

(1c-17)

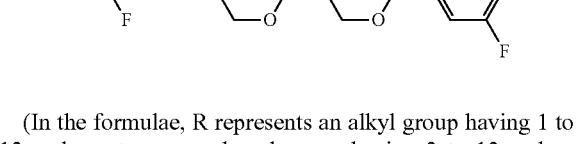

(In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

In a compound represented by the general formula (1g), R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^1$ and $Y^2$ are preferably each independently a hydrogen atom or a fluorine atom, and W is preferably a fluorine atom, a cyano group, or —$OCF_3$. The compound represented by the general formula (1g) is more preferably a compound represented by general formula (1g-1) to general formula (1g-9) below.

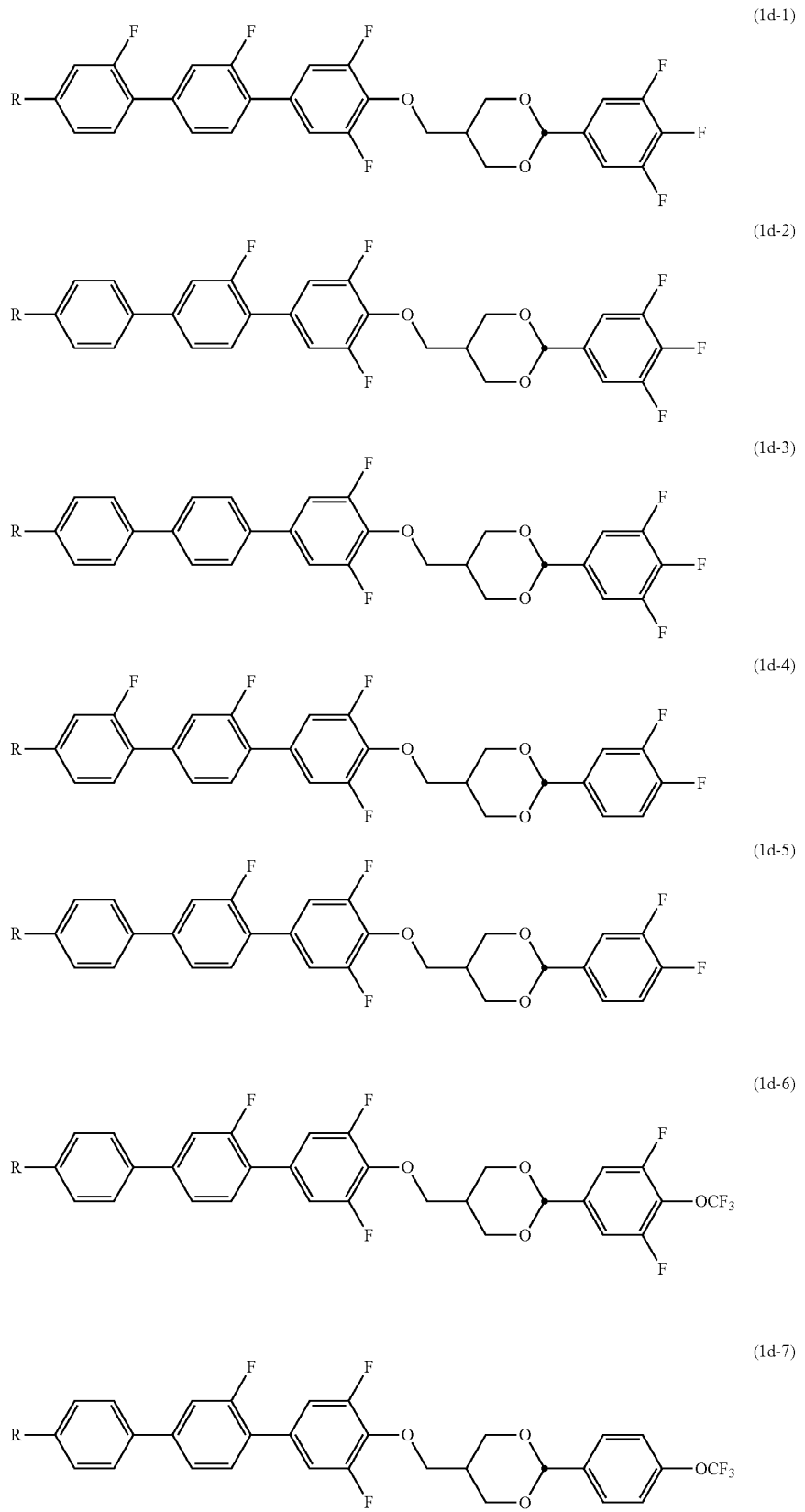

-continued (1d-8)
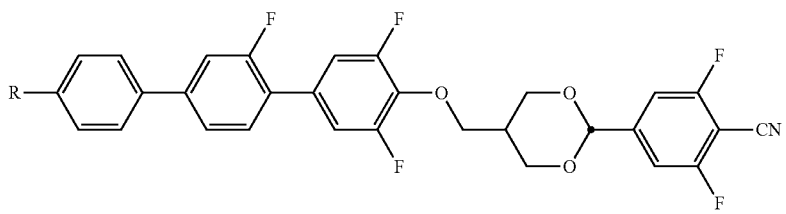

(1d-9)
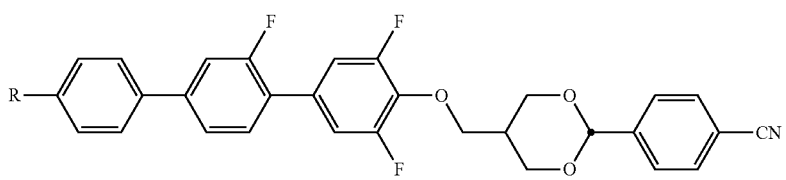

(In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

In a compound represented by the general formula. (1e), R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^1$, $Y^2$, and $Y^{12}$ preferably each independently a hydrogen atom or a fluorine atom, and W is preferably a fluorine atom or —$OCF_3$. The compound represented by the general formula (1e) is more preferably a compound represented by general formula (1e-1) to general formula (1e-8) below and further preferably general formula (1e-1) and general formula (1e-8).

[Chem. 18]

(1e-1)
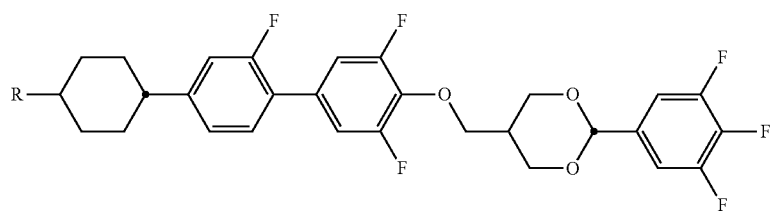

(1e-2)
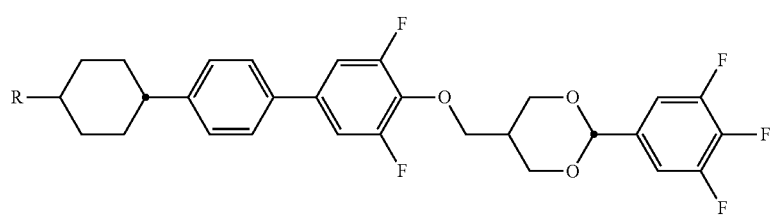

(1e-3)
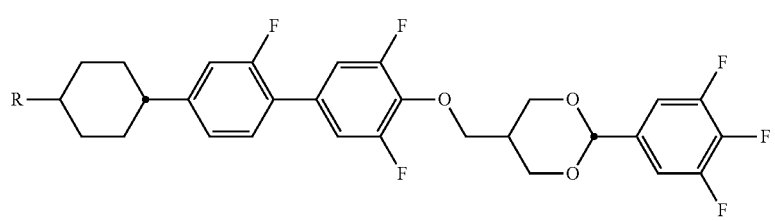

(1e-4)
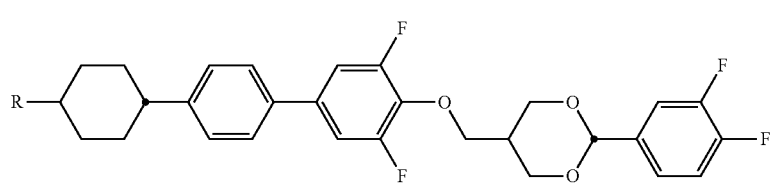

-continued (1e-5)
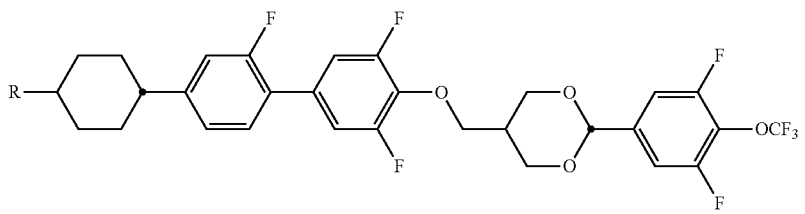

(1e-6)
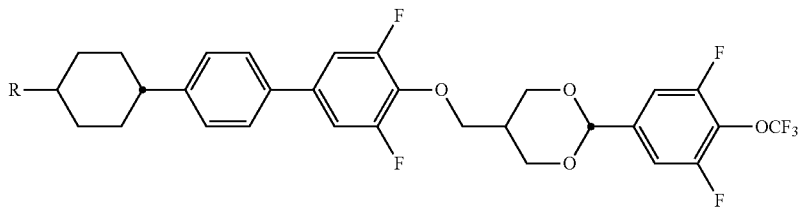

(1e-7)
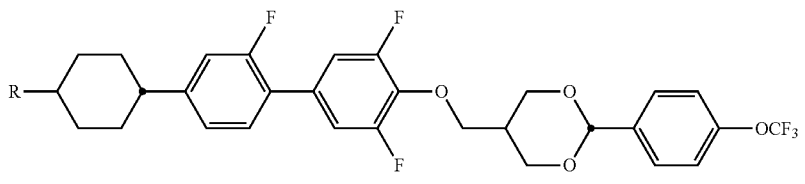

(1e-8)
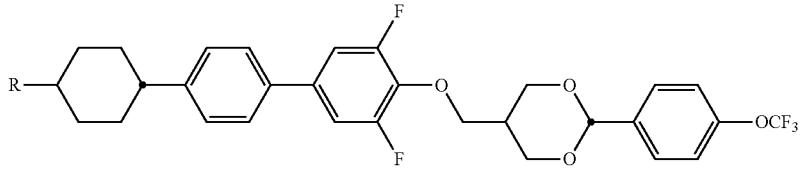

(In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

In a compound represented by the general formula (1f), R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^1$, $Y^2$, and $Y^{13}$ are preferably each independently a hydrogen atom or a fluorine atom, and W is preferably a fluorine atom or —$OCF_3$. The compound represented by the general formula (1f) is more preferably a compound represented by general formula (1f-1) to general formula (1f-8) below.

[Chem. 19]

(1f-1)
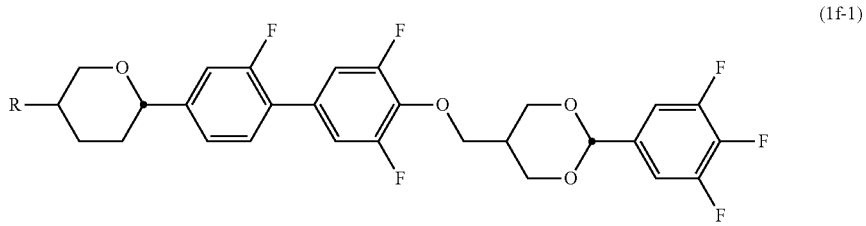

(1f-2)
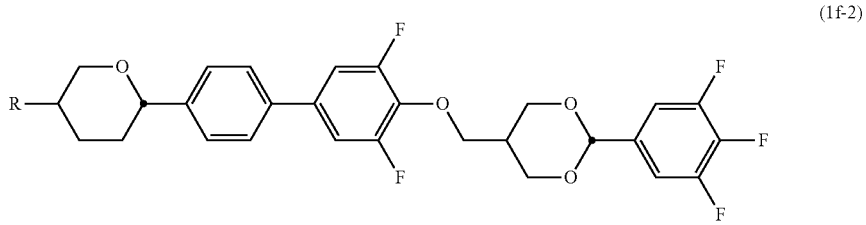

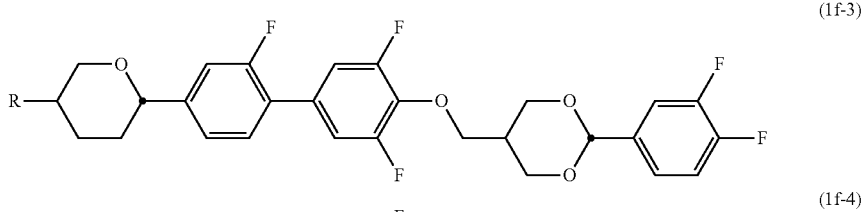
(1f-3)

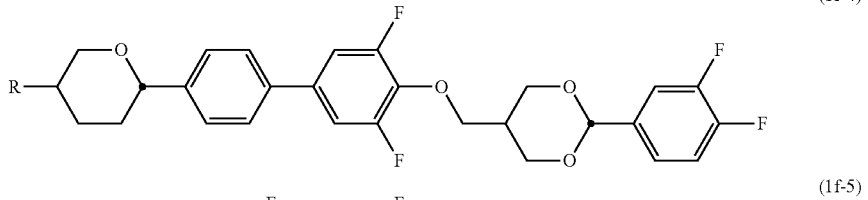
(1f-4)

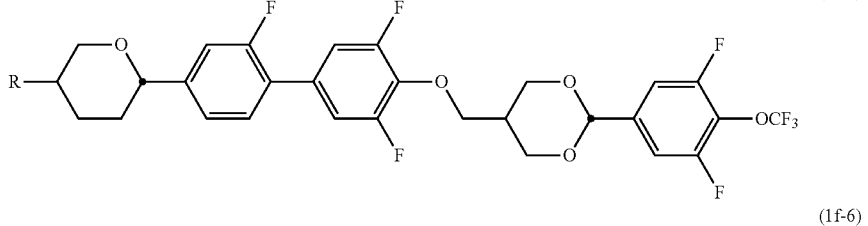
(1f-5)

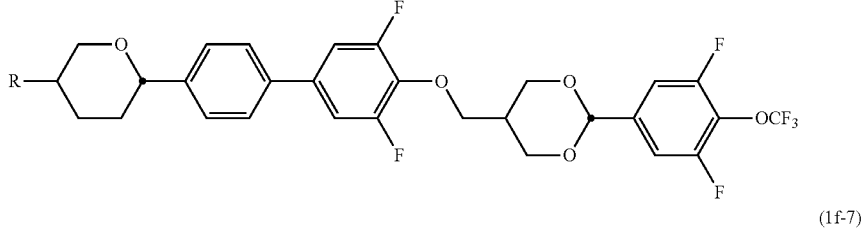
(1f-6)

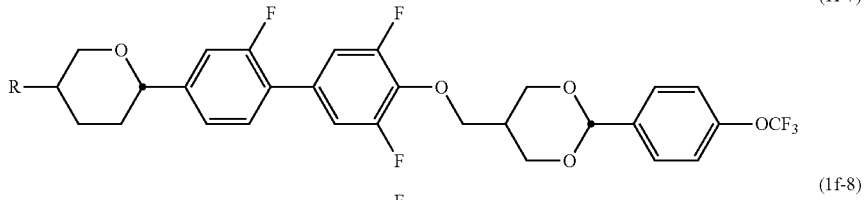
(1f-7)

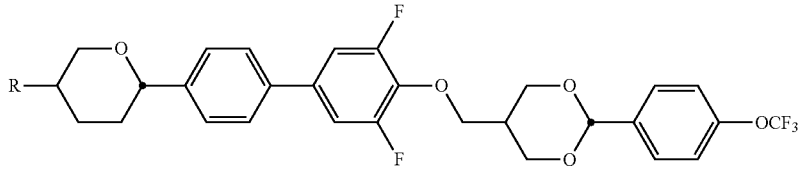
(1f-8)

In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

In a compound represented by the general formula (1g), R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^3$ to $Y^5$ are preferably each independently a hydrogen atom or a fluorine atom, and W is preferably a fluorine atom, a cyano group, or —$OCF_3$. The compound represented by the general formula (1g) is more preferably a compound represented by general formula (1g-1) to general formula (1g-6) below and further preferably general formula (1g-2).

[Chem. 20]

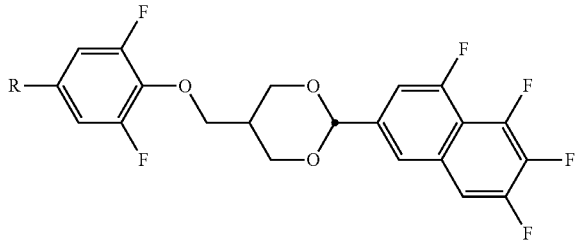
(1g-1)

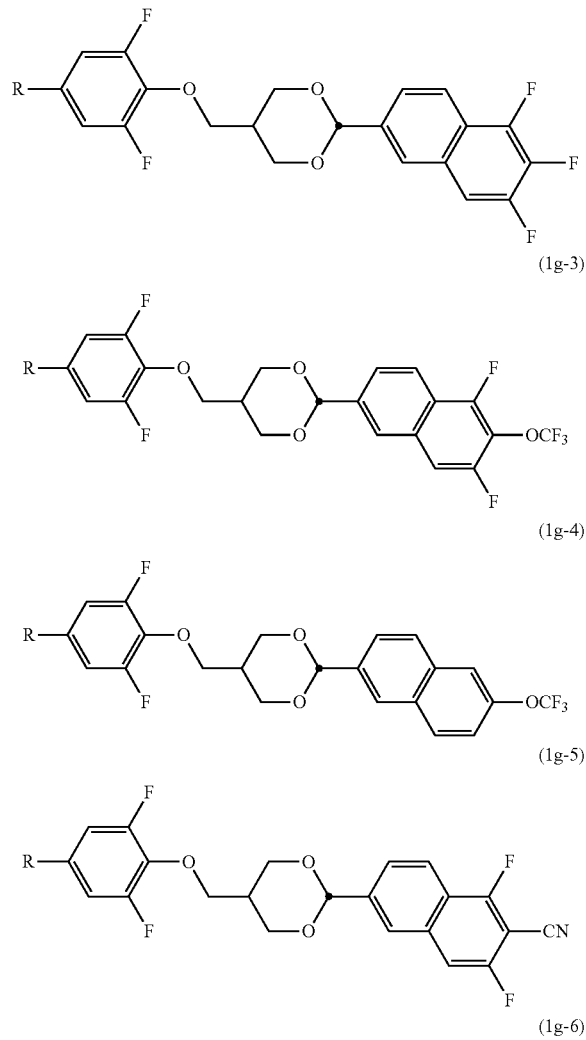

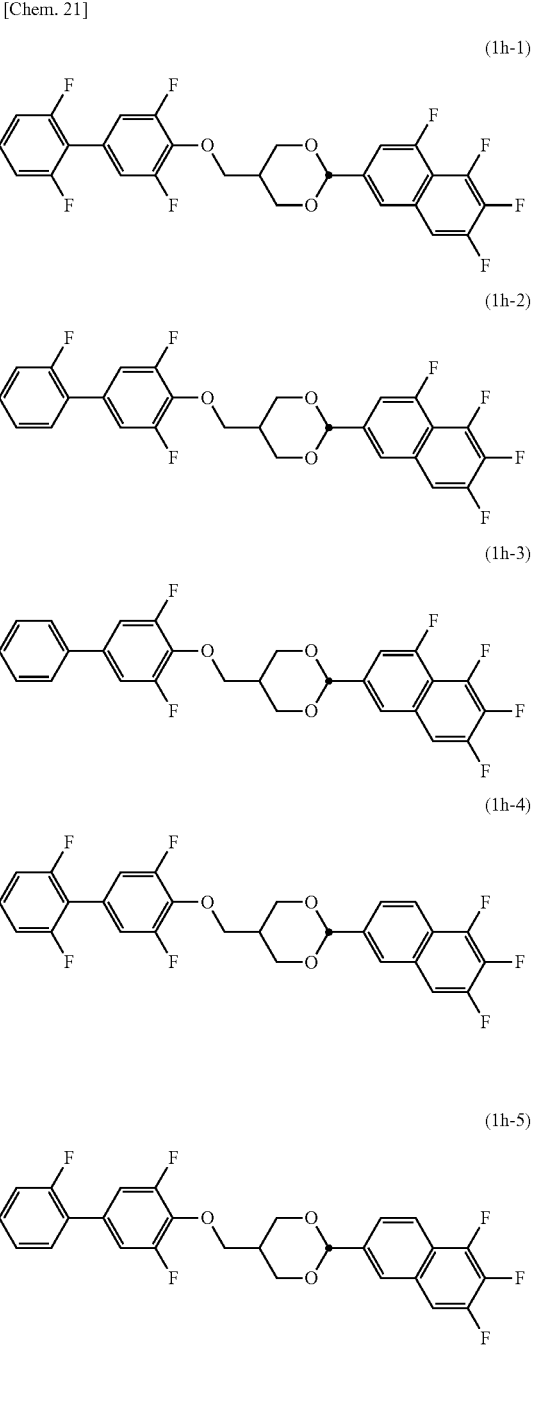

[Chem. 21]

(In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

In a compound represented by the general formula (1h), R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^3$, $Y^4Y^5$, $Y^{14}$, and $Y^{15}$ are preferably each independently a hydrogen atom or a fluorine atom, and W is preferably a fluorine atom, a cyano group or —$OCF_3$. The compound represented by the general formula (1h) is more preferably a compound represented by general formula (1h-1) to general formula (1n-12) below.

-continued

[Chem. 22]

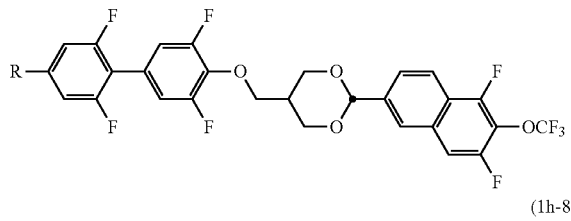
(1h-7)

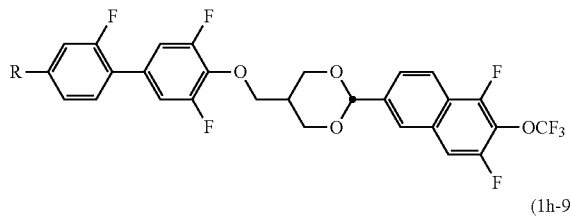
(1h-8)

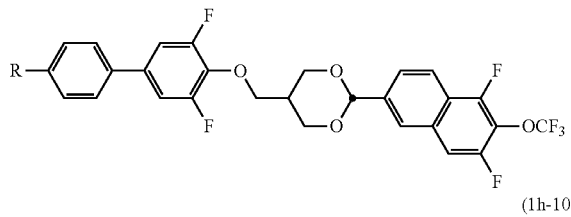
(1h-9)

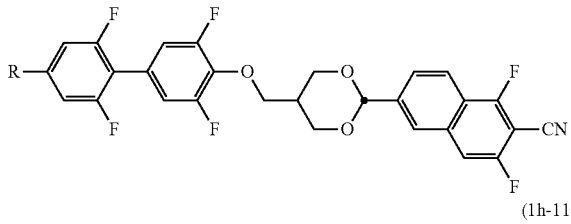
(1h-10)

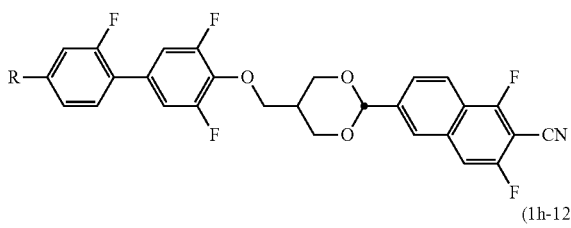
(1h-11)

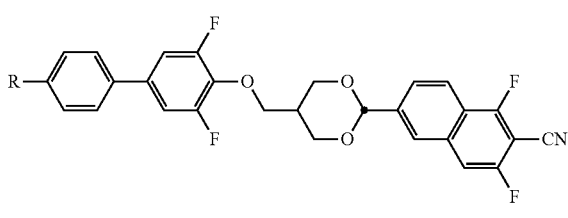
(1h-12)

(In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

In a compound represented by the general formula (1i), R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^3$ to $Y^5$ are preferably each independently a hydrogen atom or a fluorine atom, W is preferably a fluorine atom, a cyano group, or —$OCF_3$, and $A_9$ is preferably a trans-1,4-cyclohexylene group or

[Chem. 23]

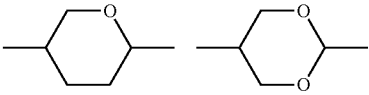

The compound represented by the general formula (1i) is more preferably a compound represented by general formula (1i-1) to general formula (1i-6) below.

[Chem. 24]

(1i-1)

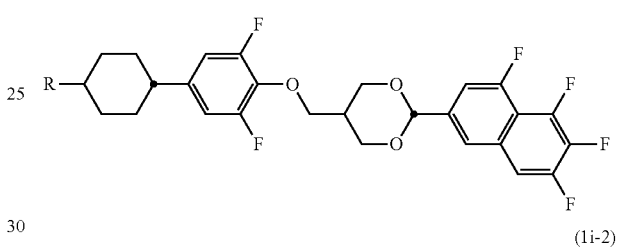

(1i-2)

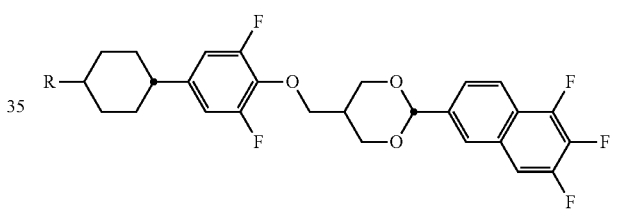

(1i-3)

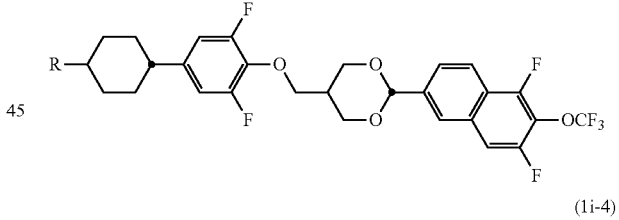

(1i-4)

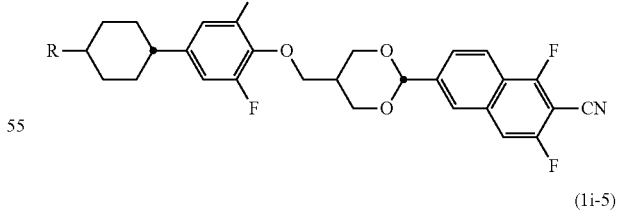

(1i-5)

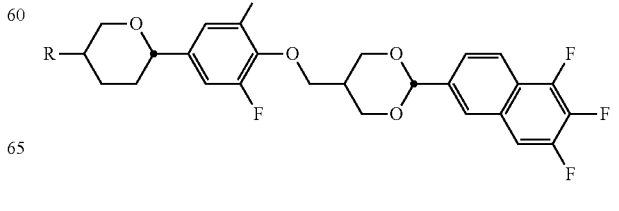

-continued

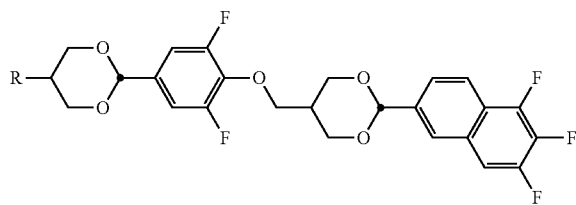
(1i-6)

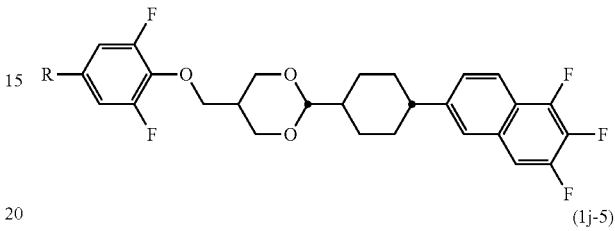
(1j-3)

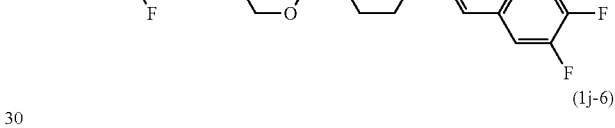
(1j-4)

(1j-5)

(1j-6)

(In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

In a compound represented by the general formula (1j), R is preferably an alkyl group having 1 to 8 carbon atoms or an alkenyl group having 2 to 8 carbon atoms, and particularly preferably an alkyl group having 1 to 5 carbon atoms or an alkenyl group having 2 to 5 carbon atoms, $Y^3$ to are preferably each independently a hydrogen atom or a fluorine atom, W is preferably a fluorine atom, and $A^9$ is preferably a 1,4-cyclohexylene group, a 1,4-phenylene group, or

[Chem. 25]

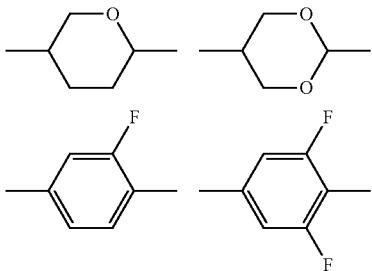

The compound represented by the general formula (1j) is more preferably a compound represented by general formula (1J-1) to general formula (1j-6) below.

[Chem. 26]

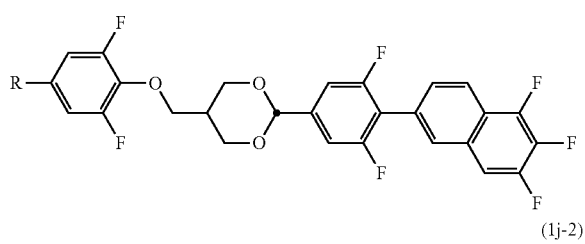
(1j-1)

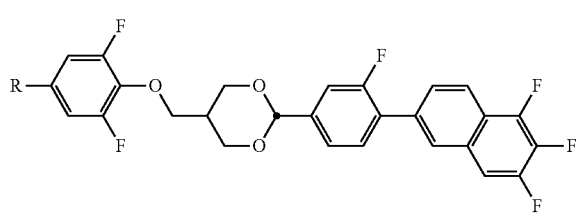
(1j-2)

(In the formulae, R represents an alkyl group having 1 to 12 carbon atoms, an akenyl group having 2 to 12 carbon atoms, an alkoxy group having 1 to 12 carbon atoms, or an alkenyloxy group having 2 to 12 carbon atoms.)

The effect of the compound represented by the general formula (1) is not exhibited at a low content in the liquid crystal composition of the present invention, and thus the composition preferably contains the compound at a content as a lower limit value of 1% by mass (hereinafter, "%" in a composition represents "% by mass") or more, preferably 2% or more, and more preferably 5% or more. Also, a high content causes the problem of precipitation or the like, and thus an upper limit value is preferably 50% or less, more preferably 30% or less, further preferably 20% or less, and particularly preferably 10% or less. Only one compound represented by the general formula (1) can be used, but two or more compounds may be simultaneously used.

A compound other than the compound represented by the general formula (1) may be used for adjusting the physical property values of the liquid crystal composition, and besides a compound having a liquid crystal phase, a compound having no liquid crystal phase can be added if required.

Typical preferred examples which can be used as a mixture with the compound represented by the general formula (1) include second to fourth components below, and the liquid crystal composition provided by the present invention preferably contains at least one compound represented by the general formula (1) as a first component and at least one of the second to fourth compounds as another component.

That is, the second component is a so-called fluorine-based (halogen-based) type liquid crystal compound, and examples thereof include compounds represented by general formulae (A1) to (A3) below.

[Chem. 27]

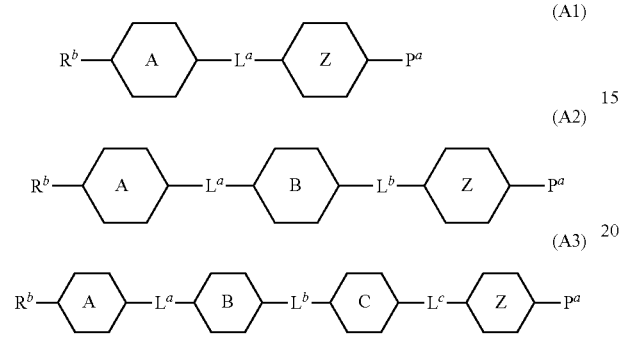

In the formulae, $R^b$ represents an alkyl group having 1 to 12 carbon atoms, which may be linear or branched and may have a 3 to 6-member ring structure, in which any desired —$CH_2$— present in the group may be substituted by —O—, —CH=CH—, —CH=CF—, —CF=CH—, —CF=CF—, or —C≡C—, and any desired hydrogen atom present in the group may be substituted by a fluorine atom or a trifluoromethoxy group, and $R^b$ is preferably a linear alkyl group having 1 to 7 carbon atoms, a linear 1-alkenyl group having 2 to 7 carbon atoms, a linear 3-alkenyl group having 4 to 7 carbon atoms, or an alkyl group having 1 to 5 carbon atoms and a terminal substituted by an alkoxy group having 1 to 3 carbon atoms. When an asymmetric carbon is produced by branching, the compound may be optically active or racemic.

Ring A, ring B, and ring C each independently represent a group selected from the group consisting of a trans-1,4-cyclohexylene group (one —$CH_2$— group or two or more unadjacent —$CH_2$— groups present in the group may be substituted by an oxygen atom), a trans-decahydronaphthalene-trans-2,6-diyl group, a 1,4-phenylene group one CH group or two or more unadjacent CH groups present in the group may be substituted by a nitrogen atom), a naphthalene-2,6-diyl group, a tetrahydronaphthalene-2,6-diyl group, and a 1,4-cyclohexenylene group, and one or two or more hydrogen atoms present in these groups may be substituted by F, Cl, CF, or $OCF_3$. Among these, the ring A, the ring B, and the ring C are preferably each independently a trans-1, 4-cyclohexylene group, a trans-decahydronaphthalene-trans-2,6-diyl group, a naphthalene-2,6-diyl group which may be substituted by a fluorine atom, or a 1,4-phenylene group which may be substituted by one or two fluorine atoms. In particular, when the ring B is a trans-1,4-cyclohexylene group or a trans-decahydronaphthalene-trans-2,6-diyl group, the ring A is preferably a trans-1,4-cyclohexylene group; when the ring C is a trans-1,4-cyclohexylene group or a trans-decahydronaphthalene-trans-2,6-diyl group, the ring B and the ring A are preferably each a trans-1,4-cyclohexylene group. In addition, the ring in (A3) is preferably a trans-1,4-cyclohexylene group.

$L^a$, $L^b$, and $L^c$ are connecting groups and each independently represent a single bond, an ethylene group (—$CH_2CH_2$—), a 1,2-propylene group (—CH($CH_3$)$CH_2$— or —$CH_2$CH($CH_3$)—), a 1,4-butylene group, —COO—, —OCO—, —$OCF_2$—, —$CF_2O$—, —CH=CH—, —CH=CF—, —CF=CH—, —CF=CF—, —C≡C—, $OCH_2$, $CH_2O$, or —CH=NN=CH—, preferably a single bond, an ethylene group, a 1,4—butylene group, —COO—, —$OCF_2$—, —$CF_2O$—, —CF=CF—, or —C≡C—, and particularly preferably a single bond or an ethylene group. In addition, at least one of $L^a$, $L^b$, and $L^c$ in (A2) and at least two of $L^a$, $L^b$, and $L^c$ in (A3) are preferably each represent a single bond.

Ring Z is an aromatic ring and represents any one of general formulae (La) to (Lc) below.

[Chem. 28]

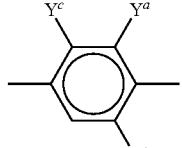

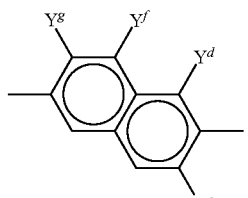

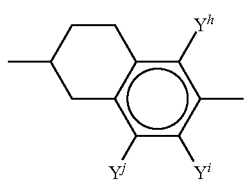

In the formulae, $Y^a$ to $Y^j$ each independently represent a hydrogen atom or a fluorine atom, at least one of $Y^a$ and $Y^b$ in (La) is preferably a fluorine atom, at least one of $Y^d$ to $Y^f$ in (Lb) is preferably a fluorine atom, particularly $Y^d$ in (Lb) is more preferably a fluorine atom, and at least one of $Y^h$ and $Y^i$ in (Lc) is preferably a fluorine atom, particularly $Y^h$ in (Lc) is more preferably a fluorine atom.

A terminal group $P^a$ represents a fluorine atom, a chlorine atom, a trifluoromethoxy group, a difluoromethoxy group, a trifluoromethyl group, a difluoromethyl group, an alkoxy group having 2 or 3 carbon atoms and substituted by two or more fluorine atoms, an alkyl, group having 2 or 3 carbon atoms and substituted by two or more fluorine atoms, an alkenyl group having 2 or 3 carbon atoms and substituted by two or more fluorine atoms, or an alkenyloxy group having 2 or 3 carbon atoms and substituted by two or more fluorine atoms, and $P^a$ is preferably a fluorine atom, a trifluoromethoxy group, or a difluoromethoxy group and particularly preferably a fluorine atom.

The third component is a so-called cyano-based p-type liquid crystal compound, and examples thereof include compounds represented by general formulae (B1) to (B3) below.

[Chem. 29]

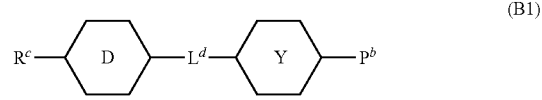
(B1)

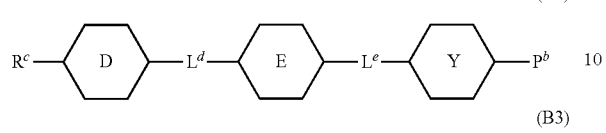
(B2)

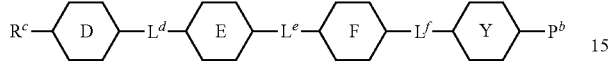
(B3)

In the formulae, $R^c$ represents an alkyl group having 1 to 12 carbon atoms, which may be linear or branched and may have a 3 to 6-member ring structure, in which any desired —$CH_2$— present in the group may be substituted by —CH=CH—, —CH=CF—, —CF=CH—, —CF=CF—, or —C≡C—, and any desired hydrogen atom present in the group may be substituted by a fluorine atom or a trifluoromethoxy group, and $R^c$ is preferably a linear alkyl group having 1 to 7 carbon atoms, a linear 1-alkenyl group having 2 to 7 carbon atoms, a linear 3-alkenyl group having 4 to 7 carbon atoms, or an alkyl group having 1 to 5 carbon atoms and a terminal substituted by an alkoxy group having 1 to 3 carbon atoms. When an asymmetries carbon produced by branching, the compound may be optically active or racemic.

Ring D, ring E, and ring F each independently represent a group selected from the r up consisting of a trans-1,4-cyclohexylene group (one $CH_2$ group or two or more unadjacent $CH_2$ groups present in the group may be substituted by an oxygen atom), a trans-decahydronaphthalene-trans-2,6-diyl group, a 1,4-phenylene group (one CH group or two or more unadjacent CH groups present in the group may be substituted by a nitrogen atom), a naphthalene-2,6-diyl group, a tetrahydronaphthalene-2,6-diyl group, and a 1,4-cyclohexenylene group, and one or two or more hydrogen atoms present in these groups may be substituted by F, Cl, $CF_3$, or $OCF_3$. Among these, the ring D, the ring E, and the ring F are preferably each independently a trans-1,4-cyclohexylene group, a trans-decahydronaphthalene-trans-2,6-diyl group, a naphthalene-2,6-diyl group which may be substituted by a fluorine atom, or a 1,4-phenylene group which may be substituted by one or two fluorine atoms. In particular, when the ring E is a trans-1,4-cyclohexylene group or a trans-decahydronaphthalene-trans-2,6-diyl group, the ring D is preferably a trans-1,4-cyclohexylene group; when the ring F is a trans-1,4-cyclohexylene group or a trans-decahydronaphthalene-trans-2,6-diyl group, the ring D and the ring E are preferably each a trans-1,4-cyclohexylene group. In addition, the ring D in (B3) is preferably a trans-1,4-cyclohexylene group.

$L^d$, $L^e$, and $L^f$ are connecting groups and each independently represent a single bond, an ethylene group (—$CH_2CH_2$—), a 1,2-propylene group (—CH($CH_3$)$CH_2$— or —$CH_2$CH($CH_3$)—), a 1,4—butylene group, —COO—, —OCO—, —$OCF_2$—, —$CF_2O$—, —CH=CH—, —CH=CF—, —CF=CH—, —CF=CF—, —C≡C—, -O$CH_2$—, —$CH_2$O—, or —CH=NN=CH—, preferably a single bond, an ethylene group, —COO—, —$OCF_2$—, —$CF_2O$—, —CF=CF—, or —C≡C—, and particularly preferably a single bond, an ethylene group, or —COO—. In addition, at least one of $L^d$, $L^e$, and $L^f$ in the general formula (B2) and at least two of $L^d$, $L^e$, and $L^f$ in the general formula (P3) are preferably each represent a single bond.

$P^b$ represents a cyano group.

Ring Y is an aromatic ring and represents any one of general formulae (Ld) to (Lf) below.

[Chem. 30]

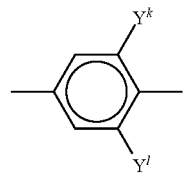
(Ld)

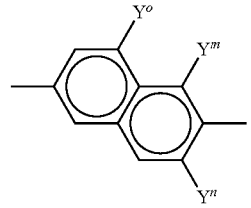
(Le)

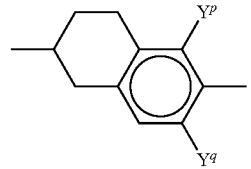
(Lf)

In the formulae, $Y^k$ to $Y^q$ each independently represent a hydrogen atom or a fluorine atom, at least one of $Y^k$ and $Y^l$ in (Ld) preferably a fluorine atom, at least one of $Y^m$ to $Y^o$ in (Le) is preferably a fluorine atom, particularly $Y^m$ in (Le) is more preferably a fluorine atom, and at least one of $Y^p$ and $Y^q$ in (Lf) is preferably a fluorine atom, particularly $Y^p$ in (Lf) is more preferably a fluorine atom.

The fourth component is a so-called nonpolar liquid crystal compound having a dielectric anisotropy of about zero, and examples thereof include, compounds represented by general formulae (C1) to (C3) below.

[Chem. 31]

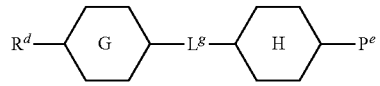
(C1)

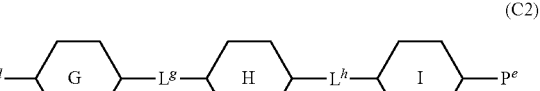
(C2)

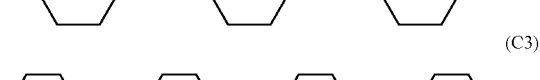
(C3)

In the formulae, $R^d$ and $P^e$ each independently represent an alkyl group having 1 to 12 carbon atoms, which may be linear or branched and may have a 3 to 6-member ring structure, in which any desired —$CH_2$— present in the group may be substituted by —O—, —CH=CH—, —CH=CF—, —CF=CH—, —CF=CF—, or —≡C—, and any desired hydrogen atom present in the group may be substituted by a fluorine atom or a trifluoromethoxy group, $R^d$ and $R^e$ are preferably each a linear alkyl group having 1 to 7 carbon atoms, a linear 1-alkenyl group having 2 to 7 carbon atoms, a linear 3-alkenyl group having 4 to 7 carbon atoms, a linear alkoxy group having 1 to 3 carbon atoms, or a linear alkyl group having 1 to 5 carbon atoms and a terminal substituted by an alkoxy group having 1 to 3 carbon atoms, and at least one of $R^d$ and $P^e$ is particularly preferably a linear alkyl group having 1 to 7 carbon atoms, a linear 1-alkenyl group having 2 to 7 carbon atoms, or a linear 3-alkenyl group having 4 to 7 carbon atoms.

Ring G, ring H, ring I, and ring J each independently represent a group selected from the group consisting of a trans-1,4-cyclohexylene group (one $CH_2$ group or two or more unadjacent $CH_2$ groups present in the group may be substituted by an oxygen atom), a trans-decahydronaphthalene-trans-2,6-diyl group, 1,4-phenylene group (one CH group or two or more unadjacent CH groups present the group may be substituted by a nitrogen atom), a naphthalene-2,6-diyl group which may be substituted by one or more fluorine atom's, a tetrahydronaphthalene-2,6-diyl group which may be substituted by one or two fluorine atoms, and a 1,4-cyclohexenylene group which may be substituted by one or two fluorine atoms. Each of the compounds preferably has less than one trans-decahydronaphthalene-trans-2,6-diyl group, naphthalene-2,6-diyl group which may be substituted by one or more fluorine atoms, tetrahydronaphthalene-2,6-diyl group which may be substituted by one or two fluorine atoms, 1,4-cyclohexenylene group which may be substituted by fluorine atoms, 1,3-dioxane—trans-2,5-diyl group, pyrimidine-2,5-diyl group, or pyridine-2,5-diyl group, and the other rings are preferably each a trans-1,4-cyclohexylene group or a 1,4-phenylene group which may be substituted by one or two fluorine, atoms or methyl groups. The total number of fluorine atoms present in the ring G, the ring H, the ring I, and the ring J is preferably 2 or less and preferably 0 or 1.

$L^g$, $L^h$, and $L^i$ are connecting groups and each independently represent a single bond, an ethylene group (—$CH_2CH_2$—) a 1,2-propylene group (—$CH(CH_3)CH_2$— or —$CH_2CH(CH_3)$—), a 1,4-butylene group, —COO—, —OCO—, —OCF$_2$—, —CF$_2$O—, —CH=CH—, —CH=CF—, —CF=CH—, —CF=CF—, —C≡C—, -OCH$_2$—, —CH$_2$O—, or —CH=NN=CH—, preferably a single bond, an ethylene group, a 1,4-butylene group, —COO—, —OCO—, —OCF$_2$—, —CF$_2$O—, —CF=CF—, —C≡C—, or —CH=NN=CH—. In addition, at least one of $L^g$, $L^h$, and $L^i$ in the general formula (C2) and at least two of $L^g$, $L^h$, and $L^i$ in the general formula (C3) are preferably each represent a single bond.

In addition, compounds represented by the general formulae (A1) to (A3) and compounds represented by the general formulae (B1) to (B3) are excluded from compounds represented by the general formulae (C1) to (C3).

The compounds represented by the general formulae (A1) to (A3), the compounds represented by the general formulae (B1) to (B3), and the compounds represented by the general formulae (C1) to (C3) do not have a structure in which heteroatoms are directly bonded to each other.

The compound represented by the general formula (1) of the present invention can be produced as follows. Of course, the gist and application range of the present invention are not limited by production examples.

(Method 1)

A compound represented by general formula (6)

[Chem. 32]

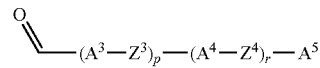

(6)

(in the formula, $A^3$, $A^4$, $Z^3$, $Z^4$, $A^5$, p, and r each independently represent the same meaning as $A^3$, $A^4$, $Z^3$, $Z^4$, $A^5$, p, and r in the general formula (1)) is subjected to dehydration condensation, in the presence of an acid catalyst, with a compound represented by general formula (7)

[Chem. 33]

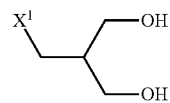

(7)

(in the formula, $X^1$ represents a chlorine atom, a bromine atom, a methanesulfonyloxy group, a p-toluenesulfonyloxy group, or a hydroxyl group), thereby producing a compound represented by general formula (2)

[Chem. 34]

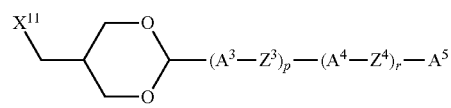

(2)

(in the formula, $A^3$, $A^4$, $Z^3$, $Z^4$, $A^5$, p, and r each independently represent the same meaning as $A^3$, $A^4$, $Z^3$, $A^5$, p, and r in the general formula (1), and $X^1$ represents a chlorine atom, a bromine atom, a methanesulfonyloxy group, p-toluenesulfonyloxy group, or a hydroxyl group).

The solvent used may be any solvent as long as it allows the reaction to preferably proceed, and the solvent is preferably an aromatic solvent such as toluene, benzene, xylene, or the like, an ether solvent such as tetrahydrofuran (THF), diethyl ether, diisopropyl ether, or the like, or a halogen-based solvent such as dichloromethane, chloroform, carbon tetrachloride, or the like, and preferably benzene, toluene, or dichloromethane.

The reaction temperature may be any temperature as long as it allows the reaction to preferably proceed, and the temperature is preferably from room temperature to the reflux temperature of the reaction solvent, and when the solvent used is azeotropic with water, the water produced by reaction is particularly preferably removed by separated and removed under reflux by using a Dean-Stark apparatus or the like.

The acid catalyst used may be any catalyst as long as it allows the reaction to preferably proceed, and the catalyst is preferably o-toluenesulfonic acid, chlorotrimethylsilane, sulfuric acid, or the like and more preferably p-toluenesulfonic acid or sulfuric acid.

Then, the compound represented by the general formula (2) in which $X^1$ represent a hydroxyl group is reacted, in the presence of an azodicarboxylic acid ester and phosphine, with a compound represented by general formula (3)

[Chem. 35]

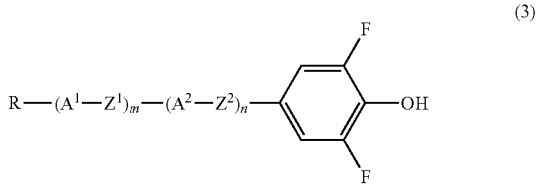

(3)

(in the formula, $A^1$, $A^2$, $Z^1$, $Z^2$, R, m, and n each independently represent the same meaning as $A^1$, $A^2$, $Z^1$, $Z^2$, R, m, and n in the general formula (1)) thereby producing the compound represented by the general formula (1).

The solvent used may be any solvent as long as it allows the reaction to preferably proceed, and the solvent is preferably an ether solvent such as THF, diethyl ether, diisopropyl ether, or the like, an aromatic solvent such as benzene, toluene, xylene, or the like, or a halogen-based solvent such as dichloromethane, chloroform, carbon tetrachloride, or the like, and more preferably THF or toluene.

The reaction temperature may be any temperature as long as it allows the reaction to preferably proceed, a temperature of −30° C. to 40° C. is preferred, a temperature of −20° C. to 20° C. is more preferred, and a temperature of −20° C. to an ice cooling temperature is particularly preferred.

The azodicarboxylic acid ester used may be any ester as long as it allows the reaction to preferably proceed, and diethyl azodicarboxylate or diisopropyl azodicarboxylate is preferred.

The phosphine used is preferably triphenylphosphine.

The compound represented by the general formula (1) can be also produced by reacting the compound represented by the general formula (2) in which $X^1$ represents a chlorine atom, a bromine atom, a methanesulfonyloxy group, or a p-toluenesulfonyloxy group, with the compound represented by the general formula (3) in the presence of a base.

The solvent used may be any solvent as long as it allows the reaction to preferably proceed, and the solvent is preferably an ether solvent such as THF diethyl ether, diisopropyl ether, or the like, an amide-based solvent such as N,N-dimethylformamide (DMF), N,N-dimethylacetamide, N-methylpyrrolidone, or the like, dimethylsulfoxide, or the like, and more preferably THF or DMF. In addition to the solvent, if required, water may be added for performing reaction.

The reaction temperature may be any temperature as long as it allows the reaction to preferably proceed, and the temperature is preferably from room temperature to the reflux temperature of the solvent, and more preferably a temperature of 40° C. to the reflux temperature of the solvent.

The base used is preferably an alkali metal hydroxide such as sodium hydroxide, potassium hydroxide, or the like, or a carbonate such as sodium carbonate, potassium carbonate, cesium carbonate, or the like, and more preferably potassium carbonate or cesium carbonate.

(Method 2)

Among compounds represented by the general formula (1), a compound represented by the general formula (1-1)

[Chem. 36]

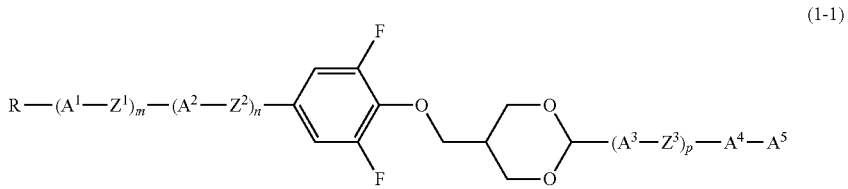

(1-1)

(in the formula, R, $A^1$, $A^2$, $A^3$, $A^6$, $Z^1$, $Z^2$, and $Z^3$ each independently represent the same meaning as R, $A^1$, $A^2$, $A^3$, $A^5$, $Z^1$, $Z^2$, and $Z^3$ in the general formula (1), $A^4$ represents a 1,4-phenylene group (a hydrogen atom present in the group may be substituted by a fluorine atom), m, n, and p each independently represent 0 or 1, and m+n+p is 0, 1, or 2) can be produced as follows. The compound represented by the general formula (3) is reacted in the presence of an azodicarboxylic acid diester and phosphine with a compound represented by general formula (4)

[Chem. 37]

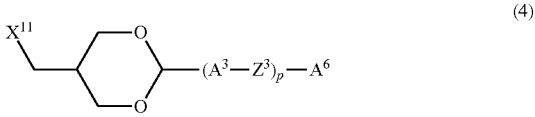

(4)

(in the formula, $A^3$, $Z^3$, and p represent the same meaning as $A^3$, $Z^3$, and p in the general formula (1-1), $X^{11}$ represents a hydroxyl group, and $A^6$ represents

[Chem. 38]

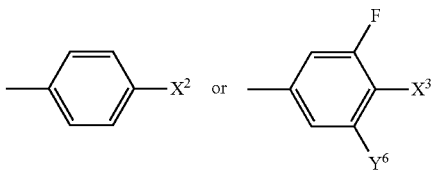

(in the formula, $X^2$ represents a chlorine atom, a bromine atom, an iodine atom, or a trifluoromethanesulfonyloxy group, $X^3$ represents a hydrogen atom, a chlorine atom, a bromine atom, an iodine atom, or a trifluoromethanesulfonyloxy group, and Y⁶ represents a hydrogen atom or a fluorine atom)), thereby producing a compound represented by general formula (5)

[Chem. 39]

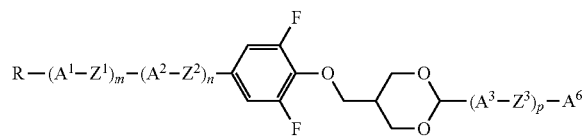
(5)

(in the formula, R, $A^1$, $A^2$, $A^3$, $Z^1$, $Z^2$, $Z^3$, m, n, and p each independently represent the same meaning as R, $A^1$, $A^2$, $A^3$, $Z^1$, $Z^2$, $Z^3$, m, n, and p in the general formula (1-1) and $A^6$ represents the same meaning as $A^6$ in the general formula (4)).

The solvent used may be any solvent as long as it allows the reaction to preferably proceed, and the solvent is preferably an ether solvent such as THF, diethyl ether, diisopropyl ether, or the like, an aromatic solvent such as benzene, toluene, xylene, or the like, or a halogen-based solvent such as dichloromethane, chloroform, carbon tetrachloride, or the like, and more preferably THF or toluene The reaction temperature may be any temperature as long as it allows the reaction to preferably proceed, and the temperature is preferably −30° C. to 40° C., more preferably −20° C. to 20° C., and particularly preferably −20° C. to an ice cooling temperature.

The azodicarboxylic acid ester used may be any ester as long as it allows the reaction to preferably proceed, and diethyl azodicarboxylate or diisopropyl azodicarboxylate is preferred.

The phosphine used is preferably triphenylphosphine.

The compound represented by general formula (5) can also be produced by reacting the compound represented by the general formula (4) in which $X^{11}$ represents a chlorine atom, a bromine atom, a methanesulfonyloxy group, or a p-toluenesulfonyloxy group with the compound represented by the general formula (3) in the presence of a base.

The reaction solvent used may be any solvent as long as it allows the reaction to preferably proceed, and the solvent is preferably an ether solvent such as THF, diethyl ether, diisopropyl ether, or the like, an amide-based solvent such as N,N-dimethylformamide (DMF), N,N-dimethylacetamide, N-methylpyrrolidone, or the like, dimethylsulfoxide, or the like, and more preferably THF or DMF. In addition to the solvent, if required, water may be added for performing reaction.

The reaction temperature may be any temperature as long as it allows the reaction to preferably proceed, and the temperature is preferably room temperature to the reflux temperature of the solvent, and more preferably 40° C. to the reflux temperature of the solvent.

The base used is preferably an alkali metal hydroxide such as sodium hydroxide, potassium hydroxide, or the like, or a carbonate such as sodium carbonate, potassium carbonate, cesium carbonate, or the like, and more preferably potassium carbonate or cesium carbonate.

Then, the compound represented by the general formula (5) is reacted in the presence of a transition metal catalyst with a compound represented by general formula (8-1) or general formula (8-2)

[Chem. 40]

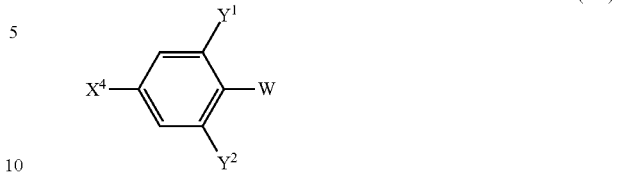

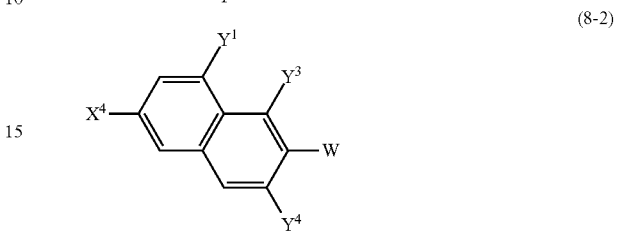

(in the formulae, $Y^1$, $Y^2$, $Y^3$, $Y^4$, $Y^5$, and W represent the same meaning as $Y^1$, $Y^2$, $Y^3$, $Y^4$, $Y^5$ and W in the general formula (1-1), and $X^4$ represents general formula (B-1) or (B-2)

[Chem. 41]

(in the formulae, $R^2$ and $R^3$ each independently represent an alkyl group which may be linear or branched and has 1 to 5 carbon atoms, E represents —$(CH_2)_s$— in which one or more hydrogen atoms present in the group may be substituted by a methyl group, and s represents 2, 3, or 4)), whereby the compound represented by the general formula (1-1) can be produced.

The solvent used may be any solvent as long as it allows the reaction to preferably proceed, and the solvent is preferably an ether solvent such as THF, diethyl ether, diisopropyl ether, or the like, an aromatic solvent such as benzene, toluene, xylene, or the like, or an amide-based solvent such as DMF, N,N-dimethylacetamide, N-methylpyrrolidone, or the like, and more preferably THF, DMF, or toluene. If required, these solvents may be used alone or as a mixture, and water may be added for allowing the reaction to preferably proceed.

The reaction temperature may be any temperature as long as it allows the reaction to preferably proceed, and the temperature is preferably from room temperature to the reflux temperature of the solvent, and more preferably a temperature of 40° C. to the reflux temperature of the solvent.

The transition metal catalyst may be any catalyst as long as it allows the reaction to preferably proceed, and the catalyst is preferably a palladium-based transition metal catalyst or nickel-based transition metal catalyst such as tetrakis(triphenylphosphine)palladium(0), palladium(II) acetate, bis(triphenylphosphine)palladium (II) dichloride,

[1,1′-bis(diphenylphosphino)ferrocene]palladium(II) dichloride, bis[di-tert-butyl (4-dimethylaminophenyl)phosphine]palladium(II) dichloride, or the like, and more preferably tetrakis(triphenylphosphine)palladium(0), palladium (II) acetate, bis[di-tert-butyl (4-dimethylaminophenyl) phosphine]palladium(II) dichloride, or [1,1′-bis(diphenylphosphino)ferrocene]palladium(II) dichloride. Also, if required, a phosphine-based ligand may be added for accelerating the progress of reaction.

(Method 3)

Among compounds represented by the general formula (1), a compound represented by general formula (1-2)

[Chem. 42]

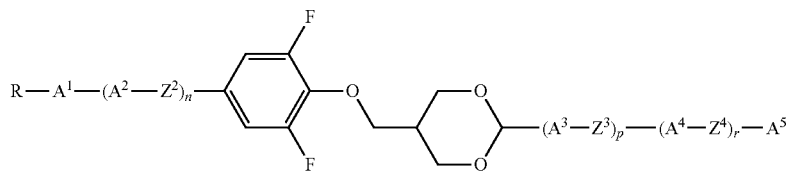

(1-2)

(in the formula, R, $A^2$, $A^3$, $A^4$, $A^5$, $Z^2$, $Z^3$, and $Z^4$ represent the same meaning as R, $A^2$, $A^3$, $A^4$, $A^5$, $Z^2$, $Z^3$, and $Z^4$ in the general formula (1), $A^1$ represents a 1,4-phenylene group (a hydrogen atom present in the group may be substituted by a fluorine atom), n, p, and r each independently represent 0 or 1, and n+p+r is 0, 1, or 2) can be produced as follows.

The compound represented by the general formula (2) in which $X^1$ represents a hydroxyl group is reacted with a compound represented by general formula (9)

[Chem. 43]

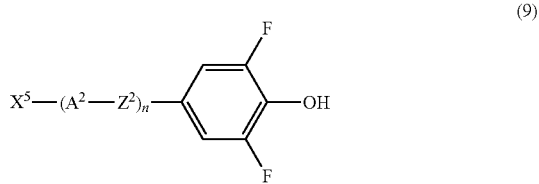

(9)

(in the formula, $X^5$ represents a chlorine atom, a bromine atom, an iodine atom, or a trifluoromethanesulfonyloxy group, and $A^2$, $Z^2$, and n represent the same meaning as $A^2$, $Z^2$, and n in the general formula (1-2)) in the presence of an azodicarboxylic acid diester and phosphine, thereby producing a compound represented by general formula (10)

[Chem. 44]

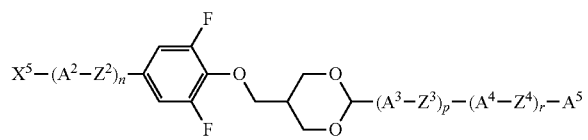

(10)

(in the formula, $X^5$ represents the same meaning as $X^5$ in the general formula (9), and $A^2$, $A^3$, $A^4$, $A^5$, $Z^2$, $Z^3$, $Z^4$, n, p, and r represent the same meaning as $A^2$, $A^3$, $A^4$, $A^5$, $Z^2$, $Z^3$, $Z^4$, n, p, and r in the general formula (1-2)).

The solvent used may be any solvent as long as it allows the reaction to preferably proceed, and the solvent is preferably an ether solvent such as THF, diethyl ether, diisopropyl ether, or the like, an aromatic solvent such as benzene, toluene, xylene, or the like, or a halogen-based solvent such as dichloromethane, chloroform, carbon tetrachloride, or the like, and more preferably THF or toluene.

The reaction temperature may be any temperature as long as it allows the reaction to preferably proceed, and the temperature is preferably −30° C. to 40° C., more preferably −20° C. to 20° C., and particularly preferably −20° C. to an ice cooling temperature.

The azodicarboxylic acid ester used may be any ester as long as it allows the reaction to preferably proceed, and diethyl azodicarboxylate or diisopropyl azodicarboxylate is preferred.

The phosphine used is preferably triphenylphosphine.

The compound represented by general formula (10) can also be produced by reacting the compound represented by the general formula (2) in which $X^1$ represents a chlorine atom, a bromine atom, a methanesulfonyloxy group, or a p-toluenesulfonyloxy group with the compound represented by the general formula (9) in the presence of a base.

The reaction solvent used may be any solvent as long as it allows the reaction to preferably proceed, and the solvent is preferably an ether solvent such as THF, diethyl ether, diisopropyl ether, or the like, an amide-based solvent such as N,N-dimethylformamide (DMF), N,N-dimethylacetamide, N-methylpyrrolidone, or the like, dimethylsulfoxide, or the like, and more preferably THF or DMF. In addition to the solvent, if required, water may be added for performing reaction.

The reaction temperature may be any temperature as long as it allows the reaction to preferably proceed, and the temperature is preferably from room temperature to the reflux temperature of the solvent, and more preferably 40° C. to the reflux temperature of the solvent.

The base used is preferably an alkali metal hydroxide such as sodium hydroxide, potassium hydroxide, or the like, or a carbonate such as sodium carbonate, potassium carbonate, cesium carbonate, or the like, and more preferably potassium carbonate or cesium carbonate.

Then, the compound represented by the general formula (10) is reacted, in the presence of a transition metal catalyst, with a compound represented by general formula (11)

[Chem. 45]

R-$A^1$$X^6$ (11)

(in the formulae, R and $A^1$ represent the same meaning as R and $A^1$ in the general formula (1-2), and $X^6$ represents general formula (B-1) or (B-2)

[Chem. 46]

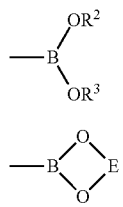

(in the formulae, R² and R³ each independently represent an alkyl group which may be linear or branched and has 1 to 5 carbon atoms, E represents —(CH$_2$)$_s$— in which one or more hydrogen atoms present in the group may be each independently substituted by a methyl group, and s represents 2, 3, or 4)), whereby the compound represented by the general formula (1-2) can be produced.

The solvent used may be any solvent as long as it allows the reaction to preferably proceed, and the solvent is preferably an ether solvent such as THF, diethyl ether, diisopropyl ether, or the like, an aromatic solvent such as benzene, toluene, xylene, or the like, or an amide-based solvent such as DMF, N,N-dimethylacetamide, N-methylpyrrolidone, or the like, and more preferably THF, DMF, or toluene. If required, these solvents may be used alone or as a mixture, and water may be added for allowing the reaction to preferably proceed.

The reaction temperature may be any temperature as long as it allows the reaction to preferably proceed, and the temperature is preferably from room temperature to the reflux temperature of the solvent, and more preferably 40° C. to the reflux temperature of the solvent is more preferred.

The transition metal catalyst may be any catalyst as long as it allows the reaction to preferably proceed, and the catalyst is preferably a palladium-based transition metal catalyst or nickel-based transition metal catalyst such as tetrakis(triphenylphosphine)palladium(0), palladium(II) acetate, bis(triphenylphosphine)palladium(II) dichloride, [1,2'-bis(diphenylphosphino)ferrocene]palladium(II) dichloride, bis[di-tert-butyl (4-dimethylaminophenyl)phosphine]palladium(II) dichloride, or the like, and more preferably tetrakis(triphenylphospine)palladium(0) palladium (II) acetate, bis[di-tert-butyl(4-dimethylaminophenyl) phosphine]palladium(II) dichloride, or [1,1'-bis (diphenylphosphino)ferrocene]palladium(II) dichloride. Also, if required, a phosphine-based ligand may be added for accelerating the progress of reaction. A liquid crystal display device using the liquid crystal composition containing the compound of the present invention satisfies both the fast response and suppressed display defects and is thus useful, particular, useful for a liquid crystal display device for active matrix driving, and can be applied to liquid crystal display device for VA-mode, PSVA-mode, PSA-mode, IPS-mode or ECE-mode.

A liquid crystal display device according to a preferred embodiment of the present invention is described in detail below with reference to the drawings.

FIG. 1 is a sectional view showing a liquid crystal display device including two substrates which are opposed to each other, a sealing material provided between the substrates, and a liquid crystal sealed in a sealed region surrounded by the sealing agent.

Specifically, FIG. 1 shows a specific configuration of the liquid crystal display device including a back plane in which a TFT layer 102 and a pixel electrode 103 are provided on a substrate a 100, and a passivation film 104 and an alignment film a 105 are provided thereon, a front plane which faces the back plane and in which a black matrix 202, a color filter 203, a planarizing film (overcoat film) 201, and a transparent electrode 204 are provided on a substrate b 200, and an alignment film b 205 is provided thereon, a sealing material 301 provided between the substrates, and a liquid crystal layer 303 sealed in a sealed region surrounded by the sealing material, projections 304 being provided on a substrate surface in contact with the sealing material 301.

A material of the substrate a or the substrate b is not particularly limited as long as it is substantially transparent, and glass, ceramic, plastic, or the like can be used. Examples of a plastic substrate which can be used include cellulose, cellulose derivatives such as triacetyl cellulose, diacetyl cellulose, and the like, polycycloolefin derivatives, polyesters such as polyethylene terephthalate, polyethylene naphthalate and the like, polyolefins such as polypropylene, polyethylene, and the like, polycarbonate, polyvinyl alcohol, polyvinyl chloride, polyvinylidene chloride, polyamide, polyimide, polyimide-amide, polystyrene, polyacrylate, polymethyl methacrylate, polyether sulfone, polyarylate, inorganic-organic composite materials such as glass fiber-epoxy resin, glass fiber-acryl resin, and the like.

When the plastic substrate is used, a barrier film is preferably provided. The barrier film has the function of decreasing moisture permeability possessed by the plastic substrate, thereby improving reliability of electric characteristic of the liquid crystal display device. The barrier film is not particularly limited as long as it has high transparency and low water vapor permeability, and a thin film formed by vapor deposition, sputtering, or chemical vapor deposition method (CVD method) using an inorganic material such as silicon oxide or the like is generally used.

In the present invention, the materials of the substrate a and the substrate b are not particularly limited, and the same material or different materials may be used. A glass substrate is preferably used because the liquid crystal display device having excellent heat resistance and dimensional stability can be produced. Also, a plastic substrate is preferred because it is suitable for a manufacturing method using a roll-to-roll method and suitable of decreasing the weight or making the substrate flexible. For the purpose of imparting flatness and heat resistance, good results can be obtained by combination of a plastic substrate and a glass substrate.

The hack plane includes the TFT layer 102 and the pixel electrode 103 which are provided on the substrate a 100. These can be produced by a general array process. The passivation film 104 and the alignment film a 105 are provided thereon to produce the back plane.

The passivation film 104 (also referred to as the "inorganic protective film") is a film for protecting the TFT film, and in general, a nitride film (SiNx), an oxide film (SiOx), or the like is formed by chemical vapor deposition (CVD) technique or the like.

In addition, the alignment film a105 is a film having the function of aligning a liquid crystal, and a polymer material such as polyimide or the like is often generally used. An alignment agent solution including a polymer material and a solvent is used as a coating solution. The alignment film may inhibit the adhesive force with the sealing material and is thus pattern-applied within the sealed region. Application is performed by using a printing method such as flexographic printing method, or a droplet discharge method such as ink let or the like. The applied alignment agent solution is crosslinked and cured by baking after the solvent is evaporated by pre-drying. Then, alignment treatment is performed for causing an alignment function.

The alignment treatment is generally performed by a rubbing method. The polymer film formed as described above is rubbed in one direction with a rubbing cloth composed of fibers of rayon or the like, thereby producing liquid crystal alignability.

Also an optical alignment method may be used. The optical alignment method is a method for producing alignability by irradiating an alignment film containing an organic material having photosensitivity with polarized light, without causing flaws and dust on the substrate, which are caused by the rubbing method. An example of the organic material used in the optical alignment method is a material containing a dichroic dye. A dichroic dye which can be used as the dichroic dye has a group (hereinafter abbreviated as an "optical alignment group") which induces molecular alignment by the Weigert effect due to dichroism or induces optical reaction as an origin of the liquid crystal alignability, such as or isomerization reaction (for example, an azobenzene group), dimerization reaction (for example, a cinnamoyl group), optical crosslinking reaction (for example, a benzophenone group), or optical decomposition reaction (for example, a polyimide group). The alignment film having alignability in a desired direction can be produced by irradiating the applied alignment agent solution with light (polarized light) having any desired deflection after evaporating the solvent by pre-drying.

On the other hand, the front plane includes the black matrix 202, the color filter 203, the planarizing film 201, the transparent electrode 204, and the alignment film b 205 which are provided on the substrate b 200.

The black matrix 202 is formed by, for example, a pigment dispersion method. Specifically, a color resin solution prepared by uniformly dispersing a black colorant for forming the black matrix is applied on the substrate b 200 provided with the barrier film 201, thereby forming a color layer. Then, the color layer is cured by baking. A photoresist is applied thereon and then pre-baked. The color layer is patterned by exposure of the photoresist through a mask pattern and then development. Then, the photoresist layer is separated, and the color layer is baked to complete the black matrix 202.

Alternatively, a photoresist-type pigment dispersion may be used. In this case, the photoresist-type pigment dispersion is applied, pre-baked, and then the color layer is patterned by exposure through a mask pattern and then development. Then, the photoresist layer is separated, and the color layer is baked to complete the black matrix 202.

The color filter 203 is formed by a pigment dispersion method, an electrodeposition method, a printing method, or a dyeing method. Take the pigment dispersion method as an example, a color resin solution prepared by uniformly dispersing a pigment (for example, red) is applied on the substrate b 202 and cured by baking, and then a photoresist is applied thereon and then pre-baked. The photoresist is patterned by exposure through a mask pattern and then development. Then, the photoresist layer is separated, and baking is again performed to complete the (red) color filter 202. The order of color filters to be formed is not particularly limited. Similarly, the green color filter 203 and the blue color filter 203 are formed.

The transparent electrode 204 is provided on the color filter 203 (if required, the overcoat layer (201) may be provided on the color filter 203 in order to flattening the surface). The transparent electrode 204 preferably has higher transparency and lower electric resistance. The transparent electrode 204 is formed by a sputtering method of forming an oxide film of ITO or the like.

Also, for the purpose of protecting the transparent electrode 204, a passivation film may be provided on the transparent electrode 204.

The alignment film b 205 is the same as the alignment film a 205.

The specific configurations of the back plane and the front plane used in the present invention are described above, but the present invention is not limited to the specific configurations, and the configurations can be freely changed according to a desired liquid crystal display device.

The share of the columnar spacers is not particularly limited, and the horizontal section thereof may have any one of various shapes such as a circular shape, polygonal shapes such as a tetragonal shape and the like. In view of a misalignment margin during a process, a horizontal section particularly preferably has a circular or regular polygonal shape. In addition, the projections preferably have the shape of a circular truncated cone or truncated pyramid.

The material of the columnar spacers is not particularly limited as long as it is insoluble in the sealing agent, the organic solvent used in the sealing agent, or the liquid crystal, and a synthetic resin (curable resin) is preferred in view of processing and weight reduction. On the other hand, the projections can be provided on the surface of the first substrate which is in contact with the sealing agent by a photolithography method or a droplet discharge method. For this reason, a photocurable resin suitable for the photolithography method or droplet discharge method is preferably used.

The case in which the columnar spacers are formed by the photolithography method is described as an example.

A resin solution (not containing a colorant) for forming the columnar spacers is applied to the transparent electrode 204 of the front plane. Then, the resin layer is cured by baking. A photoresist is applied thereon and pre-baked. The resist layer is patterned by exposure of the photoresist through a mask pattern and then development. Then, the photoresist layer is separated, and the resin layer is baked to complete the columnar spacers.

The formation positions of the columnar spacers can be determined at desired positions by the mask pattern. Therefore, both a portion inside the sealed region and a portion (sealing agent applied portion) outside the sealed region of the liquid crystal display device can be simultaneously formed. In addition, the columnar spacers are preferably formed at positions on the black matrix so as to prevent deterioration in quality of the sealed region. The columnar spacers formed by the photolithography method may be referred to as "column spacers" or "photospacers".

A mixture of a negative water-soluble resin, such as a PVA-stilbazo photosensitive resin, a polyfunctional acrylic monomer, an acrylic acid copolymer, and a triazole-based initiator is used as a material of the spacers. Another method uses a color resin prepared by dispersing a colorant in a polyimide resin. In the present invention, the material is not particularly limited, and the spacers can be formed by using a known material according to compatibility with the liquid crystal and sealing agent used.

After the columnar spacers are provided on the surface serving as the sealed region on the front plane as described above, the sealing agent (301 in FIG. 1) is applied to the surface of the back plane, the surface being in contact with the sealing agent.

The material of the sealing material is not particularly limited, and a curable resin composition prepared by adding a polymerization initiator to an epoxy-based or acryl-based photocurable, thermocurable, or photo-thermocurable resin is used. Also, a filler composed of an organic or inorganic material may be added for controlling moisture permeability, elastic modulus, and viscosity. Examples of the shape of the filler include, but not particularly limited to, a spherical shape, a fibrous shape, an amorphous shape, and the like. Further, a spherical or fibrous gap material having a monodisperse diameter may be mixed for satisfactorily controlling the cell gap, or a fibrous material which is easily entangled with the projections, on the substrate may be mixed for further enhancing the adhesive force with the substrate. In this case, the diameter of the fibrous material used is preferably about 1/5 to 1/1 of the cell gap or less, and the length of the fibrous material is preferably shorter than the seal application width.

Also, the material of the fibrous material is not particularly limited as long as a desired shape can be formed, and cellulose, a synthetic fiber such as polyamide, polyester, or the like, or inorganic material such as glass, a carbon material such as carbon, or the like can be properly selected.

A method for applying the sealing material is a printing method or a dispensing method, but the dispensing method using a small amount of the sealing material is preferred. The sealing material is generally applied at a position on the black matrix so as not to adversely affect the sealed region. The shape of the sealing material applied is a closed loop shape in order to form a liquid crystal dropping region in a next step (in order to avoid leakage of a liquid crystal).

The liquid crystal is dropped in the closed loop shape (sealed region) on the front plane to which the sealing material has been applied. The amount of the liquid crystal dropped is basically the same as the volume obtained by multiplying the height of the columnar spacers by the seal application area so as to coincide with the liquid crystal call volume. However, in order to optimize leakage of the liquid crystal in a cell bonding step and display characteristics, the amount of the liquid crystal dropped may be properly adjusted or liquid dropping positions may be dispersed.

Next, the back plane is bonded to the front plane on which the sealing material has been applied and the liquid crystal has been dropped. Specifically, the front plane and the back plane are attached to a stage having a substrate attachment mechanism such as an electrostatic chuck and arranged at a position (distance) where the alignment film b of the front plane faces the alignment film a of the back plane, and the sealing agent is not in contact with the other substrate. In this state, the pressure in the system is decreased. After the pressure is decreased, the positions of both substrates are adjusted (alignment operation) while the bond position between the front plane and the back plane is confirmed. After adjustment of the bond position is completed, the substrates are brought close to each other up to a position where the sealing material on the front plane is in contact with the back plane. In this state, the inside of the system is filled with inert gas, and the pressure is returned to normal pressure by gradually releasing the reduced pressure. In this case, the front plane is bonded to the back plane by the atmospheric pressure, forming a cell gap at the height of the columnar spacers. In this state, the sealing material is cured by irradiation with ultraviolet light to form a liquid crystal cell. Then, in some cases, curing of the sealing material is accelerated by adding a heating step. The heating step is often added for enhancing the adhesive force of the sealing material and improving the reliability of electric characteristics.

EXAMPLES

The present invention is described in further detail below by giving examples, but the present invention is not limited to these examples.

The phase transition temperature was measured by using both a polarization microscope provided with a temperature adjusting stage and a differential scanning calorimeter (DSC).

In compositions of the examples and comparative examples below, "%" represents "% by mass".

$T_{n-i}$ represents a nematic-isotropic phase transition temperature.

Compounds are described by using abbreviations below.

THF: tetrahydrofuran

Me: methyl group, Pr: n-propyl group, Bu: n—butyl group

Example 1

Production of trans-2-(3,4,5-trifluorophenyl)-5-[(2,6-difluoro-4-propylphenyloxy)methyl]-1,3-dioxane (1-1)

[Chem. 47]

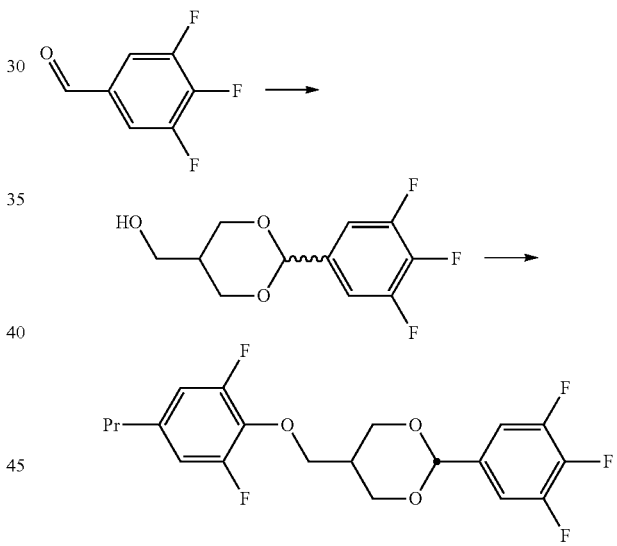

(1-1) In a nitrogen atmosphere, 3,4,5-trifluorobenzaldehyde (7.5 g), 2-hydroxymethyl-1,3-propanediol (5.0 g), and p-toluenesulfonic acid monohydrate (0.5 g) were suspended in toluene (30 mL), and stirred for 3 hours while the water produced was distilled off under reflux. After standing to cool, an aqueous saturated sodium bicarbonate solution (15 mL) was added to the mixture, followed by liquid separation. An organic layer was washed with an aqueous saturated sodium bicarbonate solution and saturated brine, and then dried by adding anhydrous sodium sulfate. The solvent was distilled off under reduced pressure to yield crude 5-hydroxymethyl-2-(3,4,5-trifluorophenyl)-1, dioxane (11.3 g).

(1-2) In a nitrogen atmosphere, 5-hydroxymethyl-2-(3,4,5-trifluorophenyl)-1,3-dioxane (11.3 g) produced in (1-1), 2,6-difluoro-4-propylphenol (7.9 g, produced by the method described in WO 2012/161170), and triphenylphosphine (13.2 g) were dissolved in THF (50 mL). Diisopropyl azodicarboxylate (9.7 g) was slowly added to the resultant solution under ice cooling, and then stirred at room temperature for 5 hours. Then, water (5 mL) was added to the mixture, the solvent was distilled off under reduced pressure, and hexane (100 mL) and toluene (20 mL) were added to prepare a suspension. An insoluble substance was filtered off, and the resultant filtrate was concentrated under reduced pressure, purified by silica gel column chromatography, and then recrystallized three times from methanol, thereby producing trans-2-(3,4,5-trifluorophenyl)-5-[(2,6-difluoro-4-propylphenyloxy)methyl]-1,3-dioxane (2.2 g).

MS m/z: 402 [M+]

Phase transition temperature (° C.) : Cr 61 Iso $^1$HNMR (CDCl$_3$, TMS internal standard) δ (ppm)=7.15 (2H, t, J=7.2 Hz), 6.71 (2H, d, J=8.8 Hz), 5.38 (1H, s), 4.39 (2H, dd, J1=4.4 Hz, J2=11.4 Hz), 3.95-3.86 (4H, m), 2.63-2.48 (3H, m), 1.64-1.55 (2H, m), 0.92 (3H, t, J=7.2 Hz)

Example 2

Production of trans-2-[4-(3,4,5-trifluorophenyl)phenyl]-5-[(2,6-difluoro-4-propylphenyloxy)methyl]-1,3-dioxane

[Chem. 48]

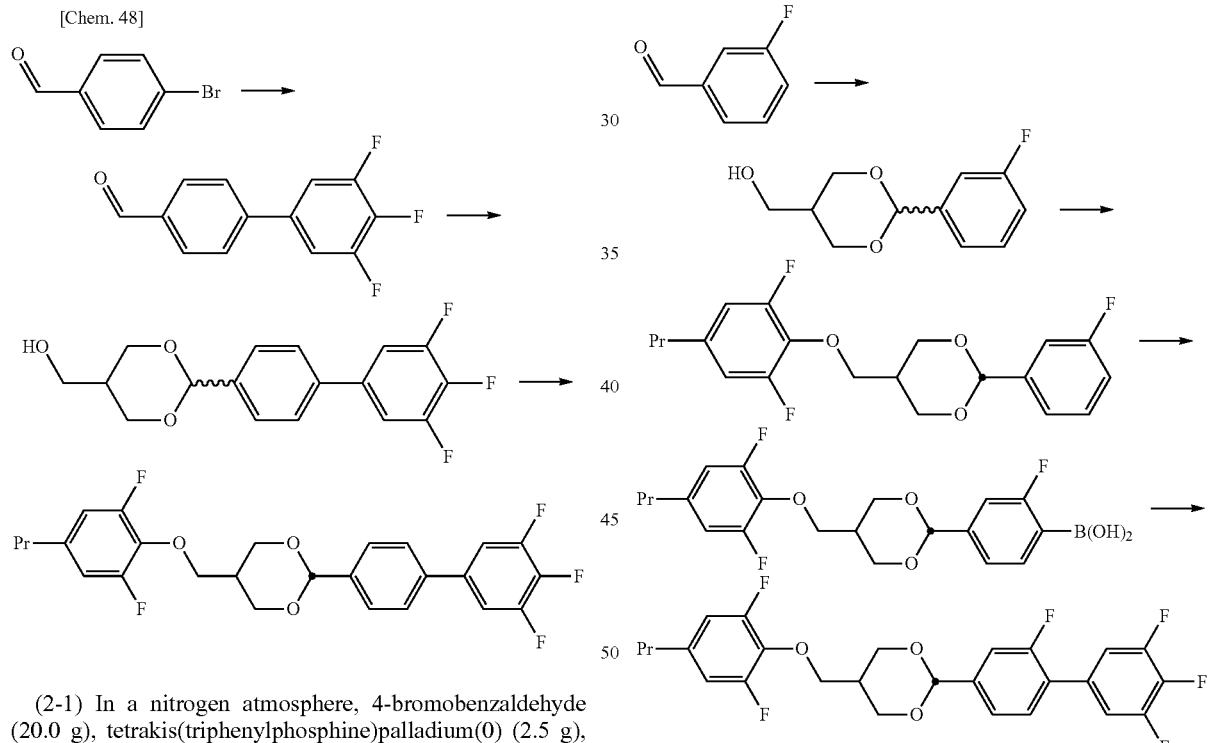

(2-1) In a nitrogen atmosphere, 4-bromobenzaldehyde (20.0 g), tetrakis(triphenylphosphine)palladium(0) (2.5 g), THF (100 mL), and a 2 mol % aqueous potassium carbonate solution (110 mL) were mixed and heated to 60° C. Then, a solution prepared by dissolving 3,4,5-trifluorphenylboric acid (20.9 g) in THF (60 mL) was slowly added under heating to the resultant mixture and stirred at 60° C. for 15 hours. After standing to cool, an insoluble substance was filtered off, toluene (30 mL) was added to the filtrate to perform liquid separation, and an organic layer was washed two times with saturated burin (100 mL) dried with anhydrous sodium sulfate. The solvent was distilled off under reduced pressure, and the residue was purified by silica gel column chromatography and recrystallized from a mixed solvent of toluene and hexane to yield 4-(3,4,5-trifluorophenyl)benzaldehyde (24.6 g).

The subsequent steps were performed by the same method as in Example 1 except that 4-(3,4,5-trifluorophenyl)benzaldehyde was used in place of 3,4,5-trifluorobenzaldehyde used in Example 1, thereby yielding trans-2-[4-(3,4,5-trifluorophenyl)phenyl]-5-[(2,6-difluoro-4-propylphenyloxy)methyl]-1,3-dioxane (15.0 g).

MS m/z: 478 [M+]

Phase transition temperature (° C.): Cr 68 SmA 129 N 137 Iso $^1$HNMR (CDCl$_3$, TMS internal standard) δ (ppm)=7.59 (2H, d, J=8.2 Hz), 7.50 (2H, d, J=8.3 Hz), 7.18 (2H, dd, J1=6.6 Hz, J2=8.6 Hz), 6.57 (2H, d, J=9.1 Hz), 5.52 (1H, s), 4.43 (2H, dd, J1=4.5 Hz, J2=11.7 Hz), 3.97-3.90 (4H, m), 2.68-2.60 (1H, m), 2.51 (2H, t, J =7.4 Hz), 1.65-1.55 (2H, m), 0.93 (3H, t, J=7.2 Hz)

Example 3

Production of trans-2-[4-(3,4,5-trifluorophenyl)-3-fluorophenyl]-5-[(2,6-difluoro-4-propylphenyloxy)methyl]-1,3-dioxane

[Chem. 49]

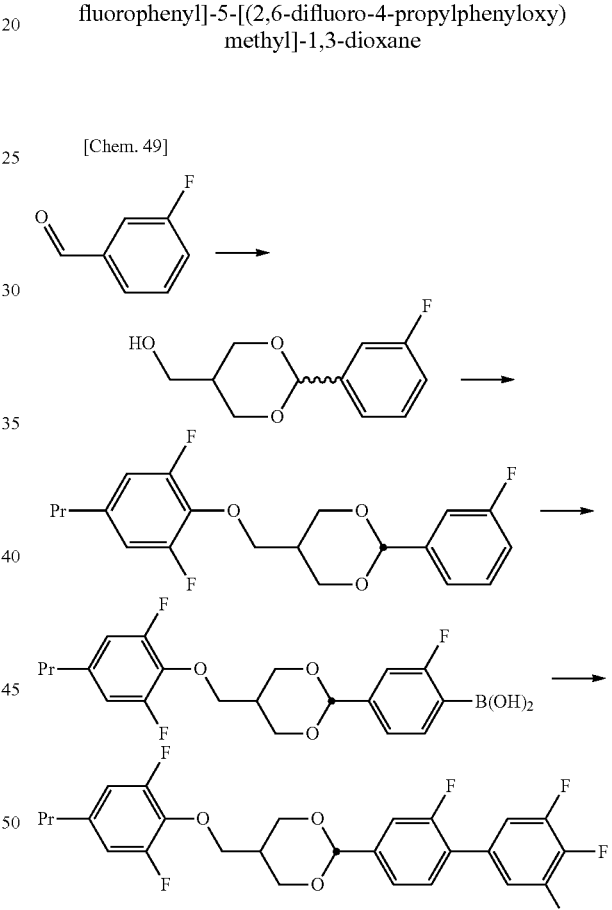

(3-1) In a nitrogen atmosphere, 3-fluorobenzaldehyde (6.0 g), 2-hydroxymethyl-1,3-propanediol (5.0 g), and p-toluenesulfonic acid monohydrate (0.5 g) were suspended in toluene (30 mL), and stirred for 3 hours while the water produced was distilled off under reflux. After standing to cool, an aqueous saturated sodium bicarbonate solution (15 mL) was added to the mixture, followed by liquid separation. An organic layer was washed with an aqueous saturated sodium bicarbonate solution and saturated brine, and then dried by adding anhydrous sodium sulfate. The solvent was distilled off under reduced pressure to yield crude 5-hydroxymethyl-2-(3-fluorophenyl)-1,3-dioxane (10.1 g).

(3-2) In a nitrogen atmosphere, 5-hydroxymethyl-2-(3-fluorophenyl)-1,3-dioxane (10.1 g) produced in (3-1), triphenylphosphine (12.7 g), and 2,6-difluoro-4-propylphenol (8.3 g) were dissolved in THF (50 mL) and cooled to 0° C., and diisopropyl azodicarboxylate (9.8 g) was slowly added dropwise to the resultant solution. Then, the resultant mixture was stirred at room temperature for 1 hour, then water (3 mL) was added to the mixture, and the solvent was distilled off under reduced pressure. Hexane (100 mL), toluene (25 mL), methanol (100 mL), and water (100 mL) were added to the residue to perform liquid separation. An organic layer was washed with water (100 mL) and saturated burin (100 mL) and dried with anhydrous sodium sulfate. The organic solvent was distilled off under reduced pressure, and the residue was purified by silica gel column chromatography, and then recrystallized three times from methanol, thereby yielding trans-2-(3-fluorophenyl)-5-(2,6-difluoro-4-propylphenyloxy)methyl-1,3-dioxane (4.5 g).

MS m/z: 366 [M+]

$^1$HNMR(CDCl$_3$, TMS internal standard) δ (ppm)=7.33-7.29 (1H, m), 7.19-7.12 (2H, m), 6.88 (1H, d, J=8.9 Hz), 6.71 (2H, d, J=8.8 Hz), 5.50 (1H, s), 4.44 (2H, dd, J1=4.3 Hz, J=11.2 Hz), 3.97-3.90 (4H, m), 2.68-2.60 (1H, m), 2.53 (2H, t, J=7.4 Hz), 1.65-1.55 (2H, m), 0.94 (3H, t, J=7.2 Hz)

(3-3) In a nitrogen atmosphere, 2-(3-fluorophenyl)-5-(2,6difluoro-4-propylphenyloxy)methyl-1,3-dioxane (16.7 g) produced in (3-2) was dissolved in THF (120 mL) and cooled to −78° C. A 1 mol/L sec-butyl lithium/hexane solution (45 mL) was slowly added to the resultant solution under cooling and stirred at −78° C. for 3 hours. Then, triisopropyl borate (11.0 g) was slowly added to the mixture, stirred at −78° C. for 1 hour, and then slowly heated to room temperature. Water (20 mL) and an aqueous saturated ammonium chloride solution (100 mL) were added to perform liquid separation. An organic layer was washed with water (100 mL) and saturated burin (100 mL) and dried by adding anhydrous sodium sulfate. The residue was recrystallized from a mixed solvent of hexane and toluene to yield 2-fluoro-4-(5-(2,6-difluoro-4-propylphenyloxymethyl-1,3-dioxan-2—yl)phenyl boric acid (9.9 g).

(3-4) In a nitrogen atmosphere, 3,4,5-trifluorobromobenzene (4.6 g), tetrakis(triphenylphosphine)palladium(0) (1.0 g), a 2 mol/L aqueous potassium carbonate solution (25 mL), and THE (40 mL) were mixed and heated to 60° C. A solution prepared by dissolving 2-fluoro-4-(5-(2,6-difluoro-4-propylphenyloxymethyl-1,3-dioxane-2—yl)phenyl boric acid (9.9 g) in THE (50 mL) was slowly added dropwise to the resultant mixture under heating and than stirred at 60° C. for 5 hours. After standing to cool to room temperature, toluene (30 mL) was added to the mixture, and an insoluble substance was removed by filtration, followed by liquid separation. An organic layer was washed two times with saturated burin (150 mL) and dried by adding anhydrous sodium sulfate. The organic solvent was distilled off under reduced pressure, and the residue was purified by silica gel column chromatography, and then recrystallized three times from an ethanol/acetone mixed solvent, thereby producing trans-2-[4-(3,4,5-trifluorophenyl)-3-fluorophenyl]-5-[(2,6-difluoro-4-propylphenyloxy)methyl]-1,3-dioxane (5.4 g).

MS m/z: 496 [M+]

$^1$-(CDCl$_3$, TMS internal standard) δ (ppm)=7.29-7.25 (1H, m), 7.17 (2H, dd, J1=6.6 Hz, J2 =8.5 Hz), 7.06-6.97 (2H, m), 6.59 (2H, d, J=9.0 Hz), 5.50 (1H, s), 4.44 (2H, dd, J1=4.3 Hz, J2 =11.2 Hz), 3.97-3.90 (4H, m), 2.68-2.60 (1H, m), 2.53 (2H, t, J =7.4 Hz), 1.65-1.55 (2H, m), 0.94 (3H, t, J=7.2 Hz)

Example 4

Production of trans-2-[4-(3,4 5-trifluorophenyl)-3,5-difluorophenyl]-5-[(2,6-difluoro-4-propylphenyloxy)methyl]-1,3-dioxane

[Chem. 50]

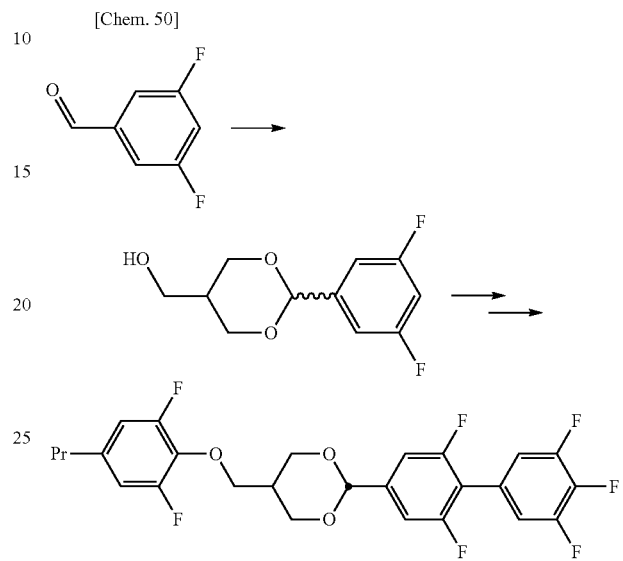

(4-1) Trans-2-[4-(3,4,5-trifluorophenyl)-3,5-difluorophenyl]-5-[(2,6-difluoro-4-propylphenyloxy)methyl]-1,3-dioxane was produced by the same method as described in Example 3 except that 3,5-difluorobenzadehyde was used in place of 3-fluorobenzaldehyde used in Example 3.

MS m/z: 514 [M+]

$^1$HNMR (CDCl$_3$, TMS internal standard) δ (ppm)=7.11 (2H, t, J=7.6 Hz), 6.86 (2H, d, J=9.3 Hz), 6.71 (2H, d, J=9.2 Hz), 5.50 (1H, s), 4.44 (2H, dd, J1=4.3 Hz, J2=11.4 Hz), 3.97-3.90 (4H, m), 2.68-2.60 (1H, m), 2.51 (2H, t, J=7.4 Hz), 1.65-1.55 (2H, m), 0.93 (3H, t, J=7.2 Hz)

Example 5

Production of trans-2-(5,6,7-trifluoronaphthalen-2-yl)-5-[(2,6-difluoro-4-propylphenyloxy)methyl]-1,3-dioxane

[Chem. 51]

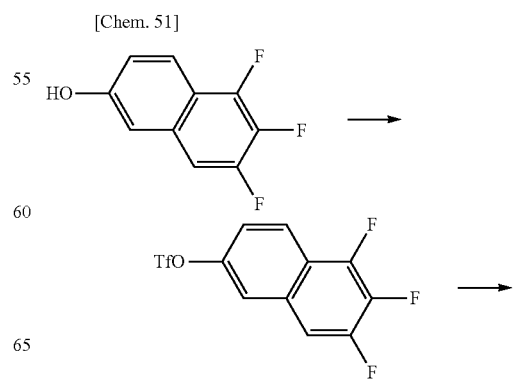

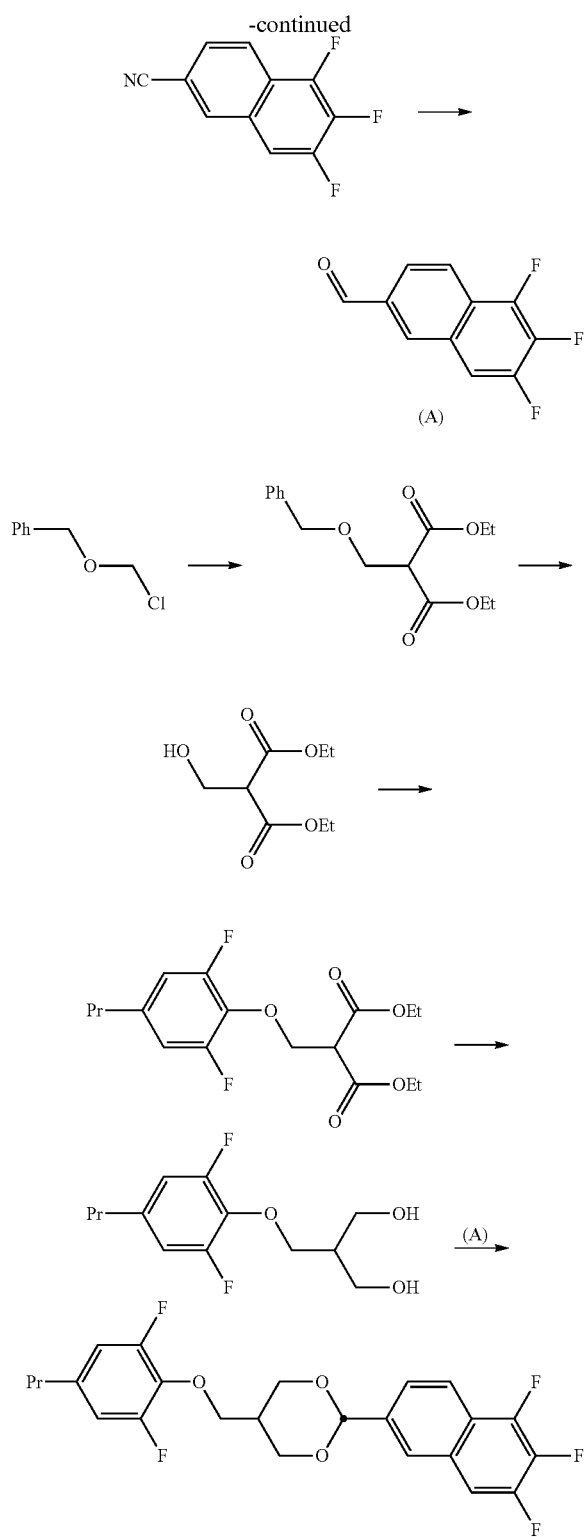

(5-1) In a nitrogen atmosphere, 5,6,7-trifluoro-2-naphthol (50 g, produced according to Japanese Unexamined Patent Application Publication No. 2004-91361) and pyridine (24.0 g) were dissolved in dichloromethane (250 mL) and ice-cooled. A solution prepared by dissolving trifluoromethanesulfonic anhydride (78.5 g) in dichloromethane (150 mL) was slowly added dropwise to the resultant solution under ice cooling. After stirring at room temperature 3 hours, 1 mol/L hydrochloric acid (200 mL) was added to the resultant mixture under ice cooling to perform liquid separation. An organic layer was washed with water (200 mL), an aqueous saturated sodium bicarbonate solution (200 mL), and saturated brine (200 mL), and then dried by adding anhydrous sodium sulfate. The organic solvent was distilled off under reduced pressure, and then the residue was purified by silica gel column chromatography to yield 5,6,7-trifluoro-naphthalen-2-yl trifluoromethanesulfonate (82.1 g).

(5-2) In a nitrogen atmosphere, a solution prepared by suspending in acetonitrile (270 mL) 5,6,7-trifluoro-naphthalen-2-yl trifluoromethanesulfonate (60 g) produced in (5-1), potassium cyanide (23.7 g), bis(triphenylphosphine) nickel (II) dibromide (6.3 g), triphenylphosphine (4.8 g), and metal zinc (1.2 g) was heated to 80° C. and stirred for 16 hours. After cooling to room temperature, water (150 mL) and toluene (100 mL) were added to the solution to perform liquid separation. An organic layer was washed two times with water (100 mL). Then, a 70% aqueous tert-butyl hydroperoxide solution (8 mL) was added to the organic layer and stirred at room temperature for 1 hour. Liquid separation was performed, and an organic layer was washed with saturated burin (100 mL) and dried with anhydrous sodium sulfate. The solvent was distilled off under reduced pressure, and then the residue was purified by silica gel column chromatography and recrystallized from ethanol to yield 2-cyano-5,6,7-trifluoronaphthalene (17.0 g).

(5-3) In a nitrogen atmosphere, 2-cyano-5,6,7-trifluoronaphthalene (17.0 g) produced in (5-2) was dissolved in toluene (350 mL), and a 1.5 mol/L diisobutyl aluminum hydride toluene solution (58 mL) was slowly added to the resultant solution under ice cooling. After stirring at room temperature of 1 hour, 1 mol/L hydrochloric acid (100 mL) was added to the resultant mixture under ice cooling. After further stirring at room temperature for hour, liquid separation was performed, and an organic layer was washed with 1 mol/L hydrochloric acid (50 mL) and saturated burin (100 mL) and then passed through an aluminum column to yield crude 5,6,7-trifluoro-2-naphthaldehyde (15.1 g, A)

(5-4) In a nitrogen atmosphere, diethyl malonate (80 g) was dissolved in THF (400 mL), and a solution prepared by dissolving tert-butyloxy potassium (56.1 g) in THF (560 mL) was slowly added dropwise to the resultant solution under ice cooling. After stirring at room temperature for 3 hours, a solution prepared by dissolving benzyl=chloromethyl=ether (78.3 g) in THF (150 mL) was slowly added to the mixture under ice cooling. After stirring at room temperature for 3 hours, water (100 mL) and 1 mol/L hydrochloric acid (300 mL) were added to perform liquid separation, and ethyl acetate (300 mL) was added to an aqueous layer to perform extraction. The organic layers were combined, washed with water (300 mL), an aqueous saturated sodium bicarbonate solution (300 mL), and saturated burin (300 mL), and dried by adding anhydrous sodium sulfate. The organic solvent was distilled off under reduced pressure, and the residue was purified by silica gel column chromatography to yield crude diethyl 2-benzyloxymethylmalonate (137.0 g).

(5-5) Diethyl 2-benzyloxymethyl-malonate (137.0 g) produced in (5-4) and 5% palladium carbon (6.9 g) were suspended in ethanol (600 mL) and acetic acid (30 mL), and stirred at room temperature for 5 hours in a hydrogen atmosphere (0.3 MPa) in an autoclave. An insoluble substance was removed by filtration, and the filtrate was concentrated under reduced pressure to yield crude diethyl 2-hydroxymethyl-malonate (85.1 g).

(5-6) In a nitrogen atmosphere, diethyl 2-hydroxymethyl-malonate (85.1 g) produced in (5-4), 2,6-difluoro-4-propylphenol (76.9 g), and triphenylphosphine (129.0 g) were dissolved in THF (400 mL) and ice-cooled. Then, diisopropyl azodicarboxylate (94.8 g) was slowly added dropwise to the resultant solution under ice cooling. After stirring at room temperature for 1 hour, water (30 mL) was added to the mixture, and the organic solvent was distilled off under reduced pressure. Then, hexane (400 mL) and toluene (100 mL) were added to the residue to prepare a suspension, and an insoluble substance was removed by filtration. The filtrate was concentrated under reduced pressure, and the residue was purified by silica gel column chromatography to yield crude diethyl 2-(2,6-difluoro-4-propylphenyloxymethyl)malonate (134.6 g).

(5-7) In a nitrogen atmosphere, lithium aluminum hydride (59.4 g) was dissolved in THF (300 mL), and a solution prepared by dissolving diethyl 2-(2,6-difluoro-4-propylphenyloxymethyl)malonate (134.6 g) produced in (5-6) in THF (650 mL) was slowly added to the mixture under ice cooling, followed by stirring for 3 hours under reflux. After ice cooling, water (50 mL) was slowly added, and then hydrochloric acid (500 mL) was added to perform liquid separation. Then, toluene (100 mL) and THF (300 mL) were added to an aqueous layer to perform extraction. The organic layers were combined, washed with an aqueous saturated sodium bicarbonate solution (600 mL) and saturated burin (600 mL), and dried by adding anhydrous sodium sulfate. The solvent was distilled off under reduced pressure to yield crude 2-(2,6-difluoro-4-propylphenyloxymethyl)-1,3-propanediol (91.1 g).

(5-8) In a nitrogen atmosphere, 2-(2,6-difluoro-4-propylphenyloxymethyl)-1,3-propanediol (18.7 g) produced in (5-8), 5,6,7-trifluoro-2-naphthaldehyde (15.1 g) produced in (5-3), and p-toluenesulfonic acid monohydrate (0.7 g) were was su pended in toluene (120 mL), and stirred for 3 hours while the produced water was distilled off under reflux. After standing to cool to room temperature, an aqueous saturated sodium bicarbonate solution (80 mL) was added to perform liquid separation, and an organic layer was washed with saturated burin (80 mL) and dried by adding anhydrous sodium sulfate. The residue was purified by silica gel column chromatography, recrystallized from an ethanol-acetone mixed solvent and further recrystallized from a hexane-toluene mixed solvent to yield trans-2-(5,6,7-trifluoronaphthalene-2-yl)-5-[(2,6-difluoro-4-propylphenyloxy)methyl]-1,3-dioxane (10.1 g).

MS m/z: 514 [M+]

$^{1}$HNMR (CDCl$_{3}$, TMS internal standard) δ (ppm)=8.05 (1H, d, J=8.7 Hz), 7.87 (1H, s), 7.75 (1H, d, J=8.7 Hz), 7.40-7.34 (1H, m), 6.71 (2H, d, J=8.5 Hz), 5.35 (1H, s), 4.40 (2H, dd, J1=4.4 Hz, J2=11.3 Hz), 3.95-3.86 (4H, m), 2.63-2.48 (3H, m), 1.64-1.55 (2H, m), 0.93 (3H, t, J=7.2 Hz)

Example 6

Production of 2-(4-trifluoromethoxyphenyl)-6-[2,6-difluoro-4-(trans-4-propylcyclohexyl)phenyl)phenyloxymethyl]-1,3-dioxane

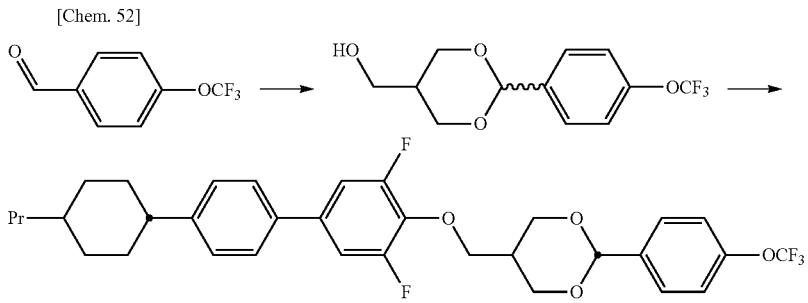

2-[4-(4—Trifluoromethoxyphenyl)phenyl]-6-[2,6-difluoro-4-(trans-4-propylcyclohexyl)phenylmethyl]-1,3-dioxane was produced by the same method as described in Examples 1 to 5.

MS m/z: 590 [M+]

$^{1}$HNMR (CDCl, TMS internal standard) δ (ppm)=7.60 (2H, d, J=8.2 Hz), 7.51 (2H, d, J=8.4 Hz), 7.47 (2H, d, J=8.4 Hz), 7.21 (2H, d, J=8.4 Hz), 7.16-7.12 (2H, m), 5.37 (1H, s), 4.41-4.37 (2H, m), 3.95-3.86 (4H, m), 2.63-2.62 (1H, m), 2.49 (1H, tt, J1=3.0 Hz, J2=12.1 Hz), 1.93-1.85 (4H, m), 1.48-1.18 (7H, m), 1.10-0.99 (2H, m), 0.90 (3H, t, J=7.1 Hz)

Comparative Example 1

Production of trans-4-[3,5-difluoro-4-(3,4,5-trifluorophenyl)phenyl]cyclohexyl-(2,6-difluoro-4-propylphenyloxy)methane

[Chem. 53]

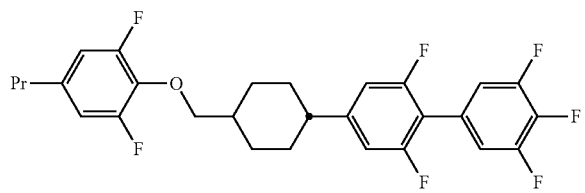

Trans-4-[3,5-difluoro-4-(3,4,5-trifluorophenyl)phenyl]cyclohexyl-(2,6-difluoro-4-propylphenyloxy)methane was produced by the method described in WO2012/161178.

Example 7

Preparation-1 of Liquid Crystal Composition

A host liquid crystal composition (H) having a composition below was prepared.

[Chem. 54]

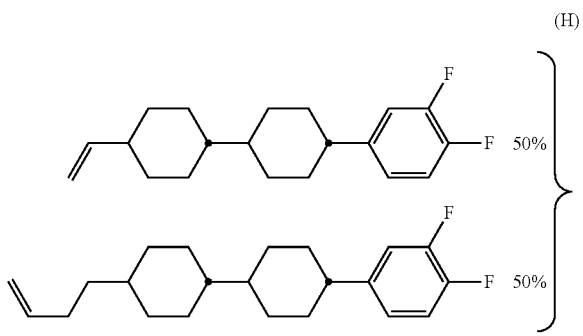

The physical property values of (H) are as follows.
Nematic phase upper limit temperature ($T_{n-i}$): 117.2° C.
Dielectric anisotropy ($\Delta\varepsilon$): 4.76
Refractive index anisotropy ($\Delta n$): 0.0873
Viscosity ($\eta_{20}$): 20.5 mPa·s A liquid crystal composition (M-A) including 85% of the host liquid crystal (H) and 15% of trans-2-(3,4,5-trifluorophenyl)-5-[(2,6-difluoro-4-propylphenyloxy)methyl]-1,3-dioxane produced in Example 1 was prepared. The physical property values of the composition are as follows.
$T_{n-i}$: 92.6° C.
$\Delta\varepsilon$: 9.66
$\Delta n$: 0.0884
$\eta_{20}$: 22.4 mPa·s The prepared liquid crystal composition (M-A) maintained a uniform nematic liquid crystal state at room temperature for 1 month or more.

Also, a liquid crystal display device produced by using the liquid crystal composition (M-A) showed excellent display characteristics and maintained stable display characteristics over a long period of time.

Example 8

Preparation-2 of Liquid Crystal Composition

A liquid crystal composition (M-B) including 85% of the host liquid crystal (H) and 15% of trans-2-[4-(3,4,5-trifluorophenyl)phenyl]-5-[(2,6-difluoro-4-propylphenyloxy)methyl]-1,3-dioxane produced in Example 2 was prepared. The physical property values of the composition are as follows.
$T_{n-i}$: 116.1° C.
$\Delta\varepsilon$: 9.65
$\Delta n$: 0.0991
$\eta_{20}$: 27.0 mPa·s The prepared liquid crystal composition (M-B) maintained a uniform nematic liquid crystal state at room temperature for 1 month or more.

Also a liquid crystal display device produced by using the liquid crystal composition (M-B) showed excellent display characteristics and maintained stable display characteristics over a long period of time.

Example 9

Preparation-3 of Liquid Crystal Composition

A liquid crystal composition (M-C) including 85% of the host liquid crystal (H) and 15% of trans-2-[4-(3,4,5-trifluorophenyl)-3-fluorophenyl]5-[(2,6-difluoro-4-propylphenyloxy)methyl]-1,3-dioxane produced in Example 3 was prepared. The physical property values of the composition are as follows.
$T_{n-i}$: 113.3° C.
$\Delta\varepsilon$: 10.28
$\Delta n$: 0.0967
$\eta_{20}$: 27.5 mPa·s The prepared liquid crystal composition (M-C) maintained a uniform nematic liquid crystal state at room temperature for 1 month or more.

Also, a liquid crystal display device produced by using the liquid crystal composition (M-C) showed excellent display characteristics and maintained stable display characteristics over a long period of time.

Example 10

Preparation-4 of Liquid Crystal Composition

A liquid crystal composition (M-D) including 90% of the host liquid crystal (H) and 10% of trans-2-[4-(3,4,5-trifluorophenyl)-3,5-difluorophenyl]-5-[(2,6-difluoro-4-propylphenyloxy)methyl]-1,3-dioxane produced in Example 4 was prepared. The physical property values of the composition are as follows.
$T_{n-i}$: 113.0° C.
$\Delta\varepsilon$: 8.97
$\Delta n$: 0.0921
$\eta_{20}$: 26.3 mPa·s The prepared liquid crystal composition (M-D) maintained a uniform nematic liquid crystal state at room temperature for 1 month or more.

Also a liquid crystal display device produced by using the liquid crystal composition (M-D) showed excellent display characteristics and maintained stable display characteristics over a long period of time.

Example 11

Preparation-5 of Liquid Crystal Composition

A liquid crystal composition (M-E) including 85% of the host liquid crystal (H) and 15% of trans-2-(5,6,7-trifluoronaphthalen-2-yl)-5-[(2,6-difluoro-4-propylphenyloxy)methyl]-1,3-dioxane produced w Example 5 was prepared. The physical property values of the composition are as follows.
$T_{n-i}$: 103.0° C.
$\Delta\varepsilon$: 10.71
$\Delta n$: 0.1017
$\eta_{20}$: 25.4 mPa·s The prepared liquid crystal composition (M-E) maintained a uniform nematic liquid crystal state at room temperature for 1 month or more.

Also, a liquid crystal display device produced by using the liquid crystal composition (M-E) showed excellent display characteristics and maintained stable display characteristics over a long period of time.

Example 12

Preparation-5 of Liquid Crystal Composition

A liquid crystal composition (M-F) including 90% of the host liquid crystal (H) and 10% of 2-(4-trifluoromethoxyphenyl)-6-[2,6-difluoro-4-(4-trans-4-propylcyclohexyl)phenyl)phenyloxymethyl]-1,3-dioxane produced in Example 6 was prepared. The physical property values of the composition are as follows.

$T_{n-i}$: 130.9° C.
$\Delta\in$: 6.13
$\Delta n$: 0.0984
$\eta_{20}$: 27.0 mPa·s The prepared liquid crystal composition (M-F) maintained a uniform nematic liquid crystal state at room temperature for 1 month or more.

Also, a liquid crystal display device produced by using the liquid crystal composition (M-F) showed excellent display characteristics and maintained stable display characteristics over a long period of time.

Comparative Example 2

Preparation-7 of Liquid Crystal Composition

A liquid crystal composition (M-G) including 85% of the host liquid crystal (H) and 15% of trans-4-[3,5-difluoro-4-(3,4,5-trifluorophenyl)phenyl]cyclohexyl-(2,6-difluoro-4-propylphenyloxy)methane produced in Comparative Example 1 was prepared. The physical property values of the composition are as follows.

$T_{n-i}$: 111.0° C.
$\Delta\in$: 9.11
$\Delta n$: 0.0951
$\eta_{20}$: 26.5 mPa·s The prepared liquid crystal composition (M-G) maintained a uniform nematic liquid crystal state at room temperature for 1 month or more.

Comparison of Examples 7 to 12 with Comparative Example 2 indicate that the compounds of the present invention effectively increase $T_{n-i}$ without degrading relatively high $\Delta\in$ and viscosity.

The invention claimed is:
1. A compound represented by general formula (1),

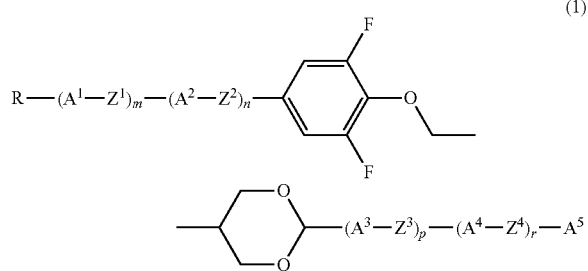

wherein in the formula (1), R represents an alkyl group having 1 to 15 carbon atoms or an alkenyl group having 2 to 15 carbon atoms, one —CH$_2$— or two or more unadjacent —CH$_2$— present in the group is/are optionally substituted by —O—, —S—, —COO—, —OCO—, or —CO—, and a hydrogen atom present in the group is optionally substituted by a fluorine atom, $A^1$, $A^2$, $A^3$, and $A^4$ each independently represent a group selected from the group consisting of
(a) a 1,4-cyclohexylene group wherein one —CH$_2$— or two or more unadjacent —CH$_2$— present in the group is/are optionally substituted by —O— or —S—;
(b) a 1,4-phenylene group wherein one —CH= or two or more unadjacent —CH= present in the group is/are optionally substituted by —N=, and a hydrogen atom present in the group is optionally substituted by a fluorine atom; and
(c) a naphthalene-2,6-diyl group wherein a hydrogen atom present in the group is/are optionally substituted by a fluorine atom, $Z^1$, $Z^2$, $Z^3$, and $Z^4$ each independently represent —CH$_2$O—, —OCH$_2$—, —CF$_2$O—, —OCF$_2$—, —CH$_2$CH$_2$—, —CF$_2$CF$_2$—, —CH=CH—, —CF=CF—, —C≡C—, or a single bond, $A^5$ represents

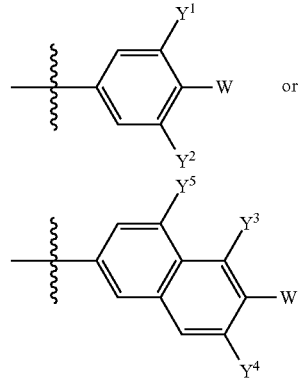

wherein in the formulae, W represents a fluorine atom, a chlorine atom, a cyano group, —CF$_3$, —OCH$_2$F, —OCHF$_2$, or —OCF$_3$, and $Y^1$, $Y^2$, $Y^3$, $Y^4$, and $Y^5$ each independently represent a fluorine atom, a chlorine atom, or a hydrogen atom, m, n, p, and r each independently represent 0 or 1, and m+n+p+r is 0, 1, 2, or 3.

2. The compound according to claim 1, wherein in the general formula (1), $A^1$, $A^2$, $A^3$, and $A^4$ each independently represent a group selected from

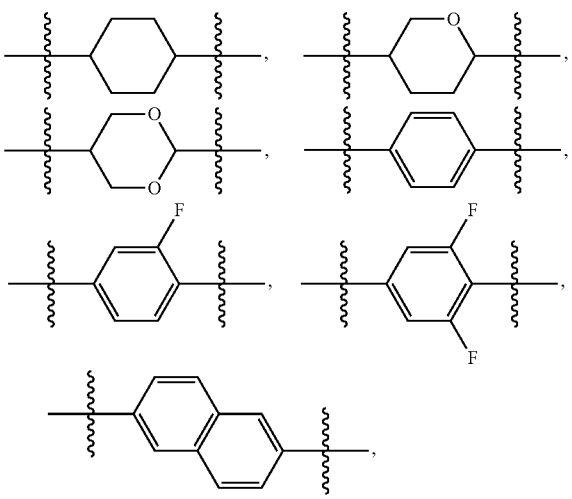

-continued

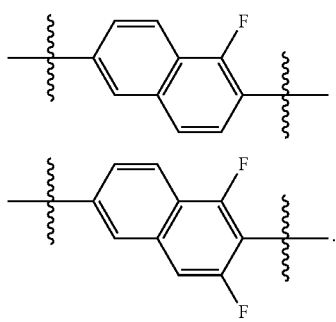
and
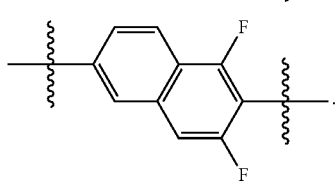

3. The compound according to claim 1, wherein in the general formula (1), $Z^1$, $Z^2$, $Z^3$, and $Z^4$ each independently represent —OCH$_2$—, —CF$_2$O—, —CH$_2$CH$_2$—, —C≡C—, or a single bond.

4. The compound according to claim 1, wherein in the general formula (1), W represents a fluorine atom, a cyano group, or —OCF$_3$.

5. The compound according to claim 1, wherein in the general formula (1), $A^5$ represents

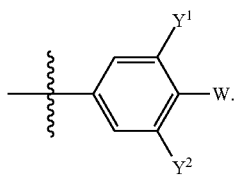

6. The compound according to claim 1, wherein in the general formula (1), $A^5$ represents

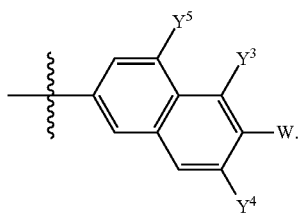

7. The compound according to claim 1, wherein the compound represented by the general formula (1) is a compound represented by general formula (1a) to general formula (1j)

(1a)
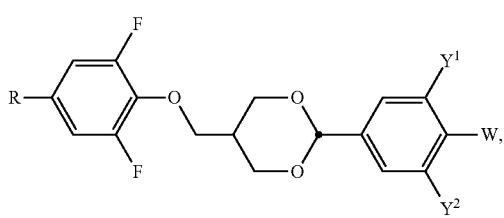

(1b)
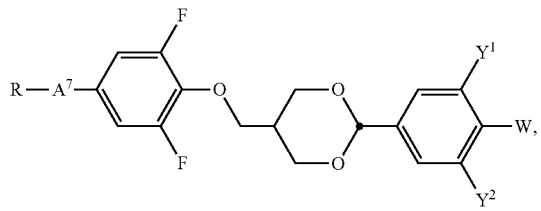

(1c)
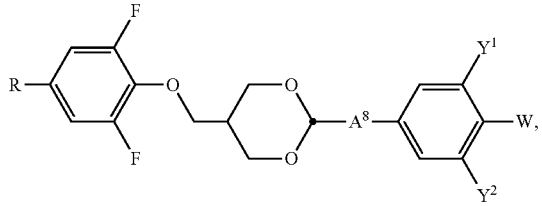

(1d)
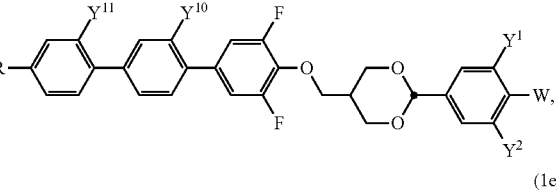

(1e)
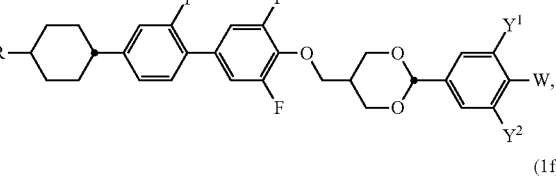

(1f)
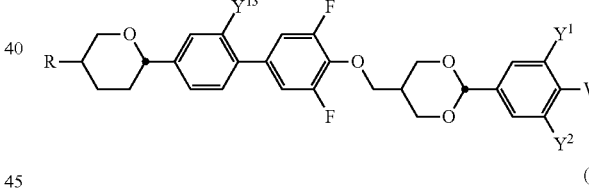

(1g)
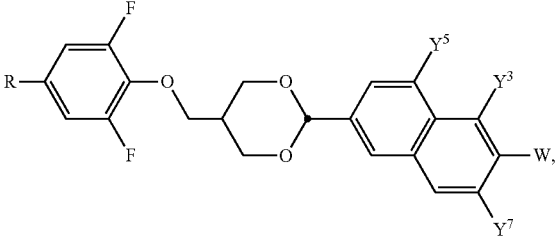

(1h)
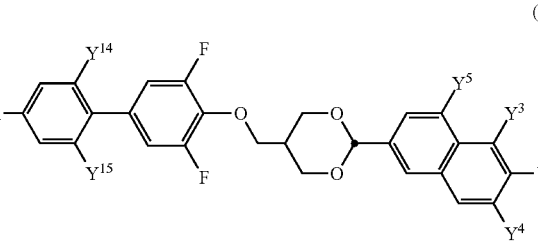

(1i)

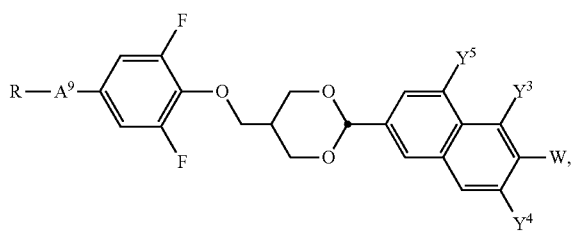

and (1j)

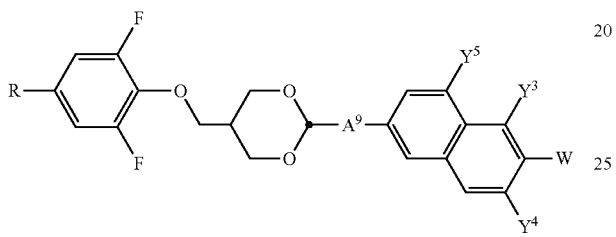

wherein in the formulae, R, W, $Y^1$, $Y^2$, $Y^3$, $Y^4$, and $Y^5$ each independently represent the same meaning as R, W, $Y^2$, $Y^3$, $Y^4$, and $Y^5$ in the general formula (1), $Y^{10}$, $Y^{11}$, $Y^{12}$, $Y^{13}$, $Y^{14}$ and $Y^{15}$ each independently represent a fluorine atom, or a hydrogen atom, and $A^7$, $A^8$, and $A^9$ each independently represent (a) 1,4-cyclohexylene group wherein one —$CH_2$— or two or more unadjacent —$CH_2$— present in the group is/are optionally substituted by —O— or —S—; or (b) 1,4-phenylene group wherein one —CH= or two or more unadjacent —CH= present in the group is/are optionally substituted by —N=, and a hydrogen atom present in the group is optionally substituted by a fluorine atom.

8. A liquid crystal composition comprising one or two or more compounds according to claim 1.

9. A liquid crystal display device using the liquid crystal composition according to claim 8.

10. A production method comprising reacting a compound represented by general formula (2)

(2)

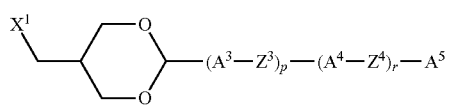

wherein in the formula, $X^1$ represents a chlorine atom, a bromine atom, a methanesulfonyloxy group, a p-toluenesulfonyloxy group, or a hydroxyl group, and $A^3$, $A^4$, $A^5$, $Z^3$, $Z^4$, p, and r each independently represent the same meaning as $A^3$, $A^4$, $A^5$, $Z^3$, $Z^4$, p, and r in the general formula (1) with a compound represented by general formula (3)

(3)

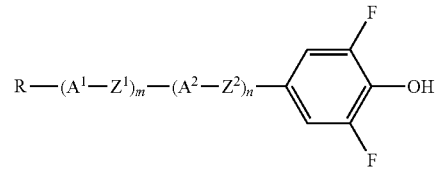

wherein in the formula, R, $A^1$, $A^2$, $Z^1$, $Z^2$, m, and n each independently represent the same meaning as R, $A^1$, $A^2$, $Z^1$, $Z^2$, m, and n in the general formula (1), thereby producing a compound represented by general formula (1), (1)

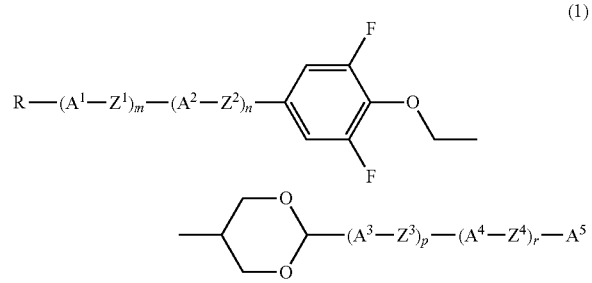

wherein in the formula, R represents an alkyl group having 1 to 15 carbon atoms or an alkenyl group having 2 to 15 carbon atoms, one —$CH_2$— or two or more unadjacent —$CH_2$— present in the group is/are optionally substituted by —O—, —S—, —COO—, —OCO—, or —CO—, and a hydrogen atom present in the group is optionally substituted by a fluorine atom, $A^1$, $A^2$, $A^3$, and $A^4$ each independently represent a group selected from the group consisting of (a) a 1,4-cyclohexylene group wherein one —$CH_2$— or two or more unadjacent —$CH_2$— present in the group is/are optionally substituted by —O— or —S—;

(b) a 1,4-phenylene group wherein one —CH= or two or more unadjacent —CH= present in the group is/are optionally substituted by —N=, and a hydrogen atom present in the group is optionally substituted by a fluorine atom; and (c) a naphthalene-2,6-diyl group wherein a hydrogen atom present in the group is optionally substituted by a fluorine atom, $Z^1$, $Z^2$, $Z^3$, and $Z^4$ each independently represent —$CH_2O$—, —$OCH_2$—, —$CF_2O$—, —$OCF_2$—, —$CH_2CH_2$—, —$CF_2CF_2$—, —CH=CH—, —CF=CF—, —C≡C—, or a single bond, $A^5$ represents

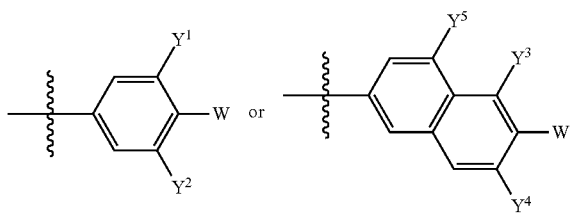

wherein in the formulae, W represents a fluorine atom, a chlorine atom, a cyano group, —$CF_3$, —$OCH_2F$, —$OCHF_2$, or —$OCF_3$, and $Y^1$, $Y^2$, $Y^3$, $Y^4$, and $Y^5$ each independently represent a fluorine atom, a chlorine atom, or a hydrogen atom, and m, n, p, and r each independently represent 0 or 1, and m+n+p+r is 0, 1, 2, or 3.

\* \* \* \* \*